(12) United States Patent
Mogna et al.

(10) Patent No.: US 10,982,184 B2
(45) Date of Patent: Apr. 20, 2021

(54) BACTERIAL STRAINS CAPABLE OF METABOLIZING OXALATES

(75) Inventors: Giovanni Mogna, Novara (IT); Gian Paolo Strozzi, Novara (IT); Luca Mogna, Novara (IT)

(73) Assignee: PROBIOTICAL S.P.A., Novara (IT)

( * ) Notice: Subject to any disclaimer, the term of this patent is extended or adjusted under 35 U.S.C. 154(b) by 0 days.

(21) Appl. No.: 14/116,996

(22) PCT Filed: May 9, 2012

(86) PCT No.: PCT/IB2012/000895
§ 371 (c)(1),
(2), (4) Date: Dec. 18, 2013

(87) PCT Pub. No.: WO2013/050831
PCT Pub. Date: Apr. 11, 2013

(65) Prior Publication Data
US 2014/0105874 A1 Apr. 17, 2014

(30) Foreign Application Priority Data
May 9, 2011 (IT) .......................... MI2011A000791

(51) Int. Cl.
| C12N 1/20 | (2006.01) |
| C12R 1/225 | (2006.01) |
| A61K 35/747 | (2015.01) |
| A61K 31/733 | (2006.01) |
| A61K 31/702 | (2006.01) |

(52) U.S. Cl.
CPC .............. *C12N 1/20* (2013.01); *A61K 31/702* (2013.01); *A61K 31/733* (2013.01); *A61K 35/747* (2013.01); *C12R 1/225* (2013.01)

(58) Field of Classification Search
None
See application file for complete search history.

(56) References Cited

U.S. PATENT DOCUMENTS

| 3,819,383 | A | 6/1974 | Ross |
| 3,819,838 | A | 6/1974 | Smith et al. |
| 4,187,321 | A | 2/1980 | Mutai |
| 4,332,790 | A | 6/1982 | Sozzi et al. |
| 4,670,272 | A | 6/1987 | Chen et al. |
| 4,853,211 | A | 8/1989 | Kurobe et al. |
| 5,071,976 | A | 12/1991 | Stirling |
| 5,343,672 | A | 9/1994 | Kearney et al. |

(Continued)

FOREIGN PATENT DOCUMENTS

| CA | 2221426 | 5/1998 |
| CA | 2739345 | 4/2010 |

(Continued)

OTHER PUBLICATIONS

Okombo et al., Urol. Res. 2010: 169-178 (2010).*
(Continued)

*Primary Examiner* — Erin M. Bowers
(74) *Attorney, Agent, or Firm* — Steinfl + Bruno, LLP

(57) ABSTRACT

A selection of strains of lactic bacteria and bifidobacteria of human intestinal origin capable of metabolizing oxalates is described. Moreover, a food composition or supplement product or pharmaceutical composition containing said bacterial strains is also described.

6 Claims, 5 Drawing Sheets

Comparison between the chromatogram for the culture medium containing 5 mM of oxalate before (A) and after (B) SPE purification.

(56) References Cited

U.S. PATENT DOCUMENTS

| | | |
|---|---|---|
| 5,413,960 A | 5/1995 | Dobrogosz et al. |
| 5,466,463 A | 11/1995 | Ford |
| 6,221,404 B1 | 4/2001 | Nguyen et al. |
| 6,262,019 B1 | 7/2001 | Keller et al. |
| 6,277,370 B1 | 8/2001 | Cavaliere et al. |
| 6,479,051 B1 | 11/2002 | Bruce et al. |
| 6,706,347 B1 | 3/2004 | Kuerzinger et al. |
| 8,257,693 B2 | 9/2012 | Ranganathan |
| 9,005,682 B2 | 4/2015 | Sprenger et al. |
| 9,125,768 B2 | 9/2015 | Husmark et al. |
| 9,492,377 B2 | 11/2016 | Mogna et al. |
| 9,883,692 B2 | 2/2018 | Hougee et al. |
| 9,925,224 B2 | 3/2018 | Mogna et al. |
| 10,028,982 B2 | 7/2018 | Mogna |
| 10,286,017 B2 | 5/2019 | Mogna et al. |
| 10,384,847 B2 | 8/2019 | Mogna |
| 2002/0022019 A1 | 2/2002 | Laulund |
| 2002/0044968 A1 | 4/2002 | Van |
| 2003/0118571 A1 | 6/2003 | Reid et al. |
| 2004/0185032 A1 | 9/2004 | Burrell |
| 2004/0208863 A1 | 10/2004 | Versalovic et al. |
| 2005/0017013 A1 | 1/2005 | Peisach et al. |
| 2005/0031814 A1 | 2/2005 | Dawes |
| 2005/0095232 A1 | 5/2005 | Volkmann |
| 2005/0220776 A1 | 10/2005 | Brondstad et al. |
| 2006/0039973 A1 | 2/2006 | Aldritt et al. |
| 2006/0121571 A1 | 6/2006 | Klaenhammer |
| 2006/0233774 A1 | 10/2006 | Lim et al. |
| 2007/0122397 A1 | 5/2007 | Sanguansri et al. |
| 2007/0148149 A1 | 6/2007 | Boettner et al. |
| 2007/0207132 A1 | 9/2007 | Speelmans et al. |
| 2007/0269515 A1 | 11/2007 | Henriksen et al. |
| 2008/0175899 A1 | 7/2008 | Ross et al. |
| 2008/0187628 A1 | 8/2008 | Champion |
| 2008/0193485 A1 | 8/2008 | Gorbach et al. |
| 2008/0299099 A1 | 12/2008 | Heczko et al. |
| 2009/0041736 A1 | 2/2009 | Sprenger et al. |
| 2009/0061164 A1 | 3/2009 | Pasbrig et al. |
| 2009/0170185 A1 | 7/2009 | Hayakawa et al. |
| 2009/0175843 A1 | 7/2009 | Gans |
| 2009/0180999 A1 | 7/2009 | Minatelli et al. |
| 2009/0226548 A1 | 9/2009 | Minatelli et al. |
| 2009/0252709 A1 | 10/2009 | Nose et al. |
| 2009/0294319 A1 | 12/2009 | Naegeli et al. |
| 2010/0003369 A1 | 1/2010 | Ter et al. |
| 2010/0092240 A1 | 4/2010 | Glasser |
| 2010/0092440 A1 | 4/2010 | Strozzi et al. |
| 2010/0168056 A1 | 7/2010 | Troup et al. |
| 2010/0278781 A1 | 11/2010 | Hougee et al. |
| 2011/0020400 A1 | 1/2011 | Macsharry et al. |
| 2011/0177198 A1 | 7/2011 | Songisepp et al. |
| 2011/0178488 A1 | 7/2011 | Balazs |
| 2011/0236360 A1 | 9/2011 | Ochi et al. |
| 2011/0274722 A1 | 11/2011 | Gorbach et al. |
| 2012/0058095 A1 | 3/2012 | Strozzi et al. |
| 2012/0195868 A1 | 8/2012 | Lathan et al. |
| 2012/0207929 A1 | 8/2012 | Yoo et al. |
| 2014/0065115 A1 | 3/2014 | Mogna et al. |
| 2014/0065116 A1 | 3/2014 | Mogna et al. |
| 2014/0072543 A1 | 3/2014 | Mogna |
| 2014/0093479 A1 | 4/2014 | Mogna et al. |
| 2014/0127164 A1 | 5/2014 | Mogna et al. |
| 2014/0231300 A1 | 8/2014 | Mogna |
| 2014/0328932 A1 | 11/2014 | Mogna |
| 2015/0017128 A1 | 1/2015 | Mogna |
| 2015/0174179 A1 | 6/2015 | Sprenger et al. |
| 2016/0106787 A1 | 4/2016 | Mogna |
| 2016/0184372 A1 | 6/2016 | Mogna |
| 2017/0014335 A1 | 1/2017 | Mogna et al. |
| 2018/0236014 A1 | 8/2018 | Mogna et al. |
| 2019/0216864 A1 | 7/2019 | Mogna et al. |
| 2020/0325440 A1 | 10/2020 | Mogna et al. |

FOREIGN PATENT DOCUMENTS

| | | |
|---|---|---|
| CA | 2739345 * | 8/2010 |
| CA | 2739345 A1 * | 8/2010 |
| CN | 1233474 A | 11/1999 |
| CN | 1345589 A | 4/2002 |
| CN | 1853508 A | 11/2006 |
| CN | 101432007 A | 5/2009 |
| CN | 101801220 A | 8/2010 |
| CN | 105163747 A | 12/2015 |
| CN | 105377277 A | 3/2016 |
| EA | 200200287 A1 | 6/2002 |
| EA | 011952 | 9/2004 |
| EA | 010981 | 2/2007 |
| EP | 0002692 | 7/1979 |
| EP | 0845350 | 6/1998 |
| EP | 0956858 | 11/1999 |
| EP | 1600060 | 11/2005 |
| EP | 1600061 | 11/2005 |
| EP | 1840205 A1 | 10/2007 |
| EP | 2000530 A1 | 12/2008 |
| EP | 2210505 A1 | 7/2010 |
| EP | 2269465 A1 | 1/2011 |
| EP | 2338976 A1 | 6/2011 |
| EP | 2360237 A1 | 8/2011 |
| EP | 2364712 A1 | 9/2011 |
| EP | 2626076 A1 | 8/2013 |
| EP | 2707477 B1 | 7/2018 |
| GB | 2396811 A | 7/2004 |
| JP | H11504049 A | 4/1999 |
| JP | 2001258549 A | 9/2001 |
| JP | 2002507123 A | 3/2002 |
| JP | 2002508762 A | 3/2002 |
| JP | 2003522731 A | 7/2003 |
| JP | 2006180836 A | 7/2006 |
| JP | 2006519014 A | 8/2006 |
| JP | 2008529535 A | 8/2008 |
| JP | 2009511506 A | 3/2009 |
| JP | 2009520470 A | 5/2009 |
| JP | 2010-511033 A | 4/2010 |
| JP | 2010187670 A | 9/2010 |
| JP | 2012527884 A | 11/2012 |
| JP | 2013009681 A | 1/2013 |
| JP | 2016518441 A | 6/2016 |
| KR | 20130038395 A | 4/2013 |
| KZ | 11784 | 8/2002 |
| KZ | 17967 | 6/2011 |
| RU | 02150268 | 6/2000 |
| RU | 2203946 C1 | 5/2003 |
| RU | 2215656 C2 | 11/2003 |
| RU | 2303058 C2 | 7/2007 |
| RU | 2316586 C2 | 2/2008 |
| RU | 2338511 C2 | 11/2008 |
| RU | 2007147945 A | 7/2009 |
| RU | 2373274 C1 | 11/2009 |
| RU | 2008118418 A | 11/2009 |
| RU | 2388479 C1 | 5/2010 |
| RU | 2445073 C2 | 3/2012 |
| RU | 2465320 C2 | 10/2012 |
| WO | 94/12142 | 6/1994 |
| WO | 1994/012142 | 6/1994 |
| WO | 97/29762 A1 | 8/1997 |
| WO | 97/29763 A1 | 8/1997 |
| WO | 99/49877 | 10/1999 |
| WO | 00/35465 A2 | 6/2000 |
| WO | 00/35465 A3 | 12/2000 |
| WO | 00/72855 | 12/2000 |
| WO | 00/72855 A2 | 12/2000 |
| WO | 03/090546 A1 | 11/2003 |
| WO | 2004/089278 | 10/2004 |
| WO | 2004/101770 | 11/2004 |
| WO | 2006/013588 A1 | 2/2006 |
| WO | 2006/073329 A1 | 7/2006 |
| WO | 2006/082824 A1 | 8/2006 |
| WO | 2006/091103 A2 | 8/2006 |
| WO | 2007/020884 A1 | 2/2007 |
| WO | 2007/029773 A1 | 3/2007 |
| WO | 2007/050656 A2 | 5/2007 |
| WO | 2007/100765 | 9/2007 |

(56) References Cited

FOREIGN PATENT DOCUMENTS

| WO | 2007/125558 | | 11/2007 |
|---|---|---|---|
| WO | 2008/038075 | | 4/2008 |
| WO | 2008/038075 | A2 | 4/2008 |
| WO | 2008/065492 | | 6/2008 |
| WO | 2008/107746 | A2 | 9/2008 |
| WO | 2008/153377 | A1 | 12/2008 |
| WO | 2009/138218 | | 11/2009 |
| WO | 2010/023248 | A1 | 3/2010 |
| WO | 2010/033768 | A1 | 3/2010 |
| WO | 2010/038714 | A1 | 4/2010 |
| WO | 2010/099824 | | 9/2010 |
| WO | 2010/103374 | | 9/2010 |
| WO | 2010103374 | A2 | 9/2010 |
| WO | 20109099824 | | 9/2010 |
| WO | WO 2010/099824 | A1 * | 9/2010 |
| WO | 2010/128084 | A1 | 11/2010 |
| WO | 2010/133761 | A1 | 11/2010 |
| WO | 2011/012932 | | 2/2011 |
| WO | 2011/017040 | | 2/2011 |
| WO | 2011/044934 | A1 | 4/2011 |
| WO | 2011/110918 | A1 | 9/2011 |
| WO | 2012/001440 | | 1/2012 |
| WO | 2012/101500 | A1 | 8/2012 |
| WO | 2012/123770 | A1 | 9/2012 |
| WO | 2012/143787 | A1 | 10/2012 |
| WO | 2012/153179 | A1 | 11/2012 |
| WO | 2010/136891 | A1 | 3/2013 |
| WO | 2013/034974 | | 3/2013 |
| WO | 2013/034974 | A1 | 3/2013 |
| WO | 2013/034975 | A1 | 3/2013 |
| WO | 2013/050831 | A1 | 4/2013 |
| WO | 2013/050833 | A1 | 4/2013 |
| WO | 2014/023995 | A1 | 2/2014 |
| WO | 2014/184639 | A1 | 11/2014 |
| WO | 2014/184643 | A1 | 11/2014 |

OTHER PUBLICATIONS

Okombo et al., Urol. Res. 2010: 169-178 (2010; published online Mar. 12, 2010).*
Baluka et al., "PCR-based detection of genes responsible for oxalate detoxification in probiotic microorganisms", Annual Meeting of the Illinois State Academy of Sciences, 2008 (https://www.eiu.edu/biology/posters/2008-11.pdf).*
Macfarlane et al., Aliment. Pharmacol. Ther. 24: 701-714 (2006).*
PCT International Search Report dated Sep. 21, 2012 for PCT/IB2012/000895 filed on May 9, 2013 in the name of Probiotical S.P.A.
PCT Written Opinion dated Sep. 21, 2012 for PCT/IB2012/000895 filed on May 9, 2013 in the name of Probiotical S.P.A.
PCT International Search Report dated Sep. 27, 2012 for PCT/IB2012/000907 filed on May 9, 2013 in the name of Probiotical S.P.A.
PCT Written Opinion dated Sep. 27, 2012 for PCT/IB2012/000907 filed on May 9, 2013 in the name of Probiotical S.P.A.
PCT International Search Report dated Aug. 24, 2012 for PCT/IB2012/000897 filed on May 9, 2013 in the name of Probiotical S.P.A.
PCT Written Opinion dated Aug. 24, 2012 for PCT/IB2012/000897 filed on May 9, 2013 in the name of Probiotical S.P.A.
Modesto, M. et al. Resistant to freezing and freeze-drying storage processes of potential probiotic bifidobacteria. Annals of Microbiology, 54 (1), pp. 43-48 (2004).
Likotrafiti, E. et al. Molecular Identification and Anti-pathogenic Activities of Putative Probiotic Bacteria Isolated from Faeces of Healthy Elderly Individuals. Microbial Ecology in Health and Disease, 16, pp. 105-112 (2004).
PCT International Preliminary Report on Patentability dated Nov. 12, 2013 for PCT/IB2012/000895 filed on May 9, 2013 in the name of Probiotical S.P.A.

PCT International Preliminary Report on Patentability dated Nov. 12, 2013 for PCT/IB2012/000897 filed on May 9, 2013 in the name of Probiotical S.P.A.
PCT International Preliminary Report on Patentability dated Nov. 12, 2013 for PCT/IB2012/000907 filed on May 9, 2013 in the name of Probiotical S.P.A.
Del Piano, M. et al. Evaluation of the intestinal colonization by microencapsulated probiotic bacteria in comparison with the same uncoated strains. Journal of Clinical Gastroenterology, vol. 44, pp. S42-S46, Sep. 2010.
Cheikhyoussef, A. et al. Antimicrobial activity and partial characterization of bacteriocin-like inhibitory substances (BLIS) produced by *Bifidobacterium infantis* BCRC 14602. Food Control, Butterworth, London, GB, vol. 20 (6), pp. 553-559, Jun. 2009.
Kim, J. et al. Antimicrobial effect of *Bifidobacteriumbreve* and *Bifidobacteriuminfantis* against *Salmonella typhimurium* KCTC 1925 and *E.coli*. Food Science and Biotechnology, Korean Society of Food Science and Technology, vol. 11 (1), pp. 89-92, Jan. 2002.
Candela, M. et al. Interaction of probiotic *Lactobacillus* and *Bifidobacteriun* strains with human intestinal epithelial cells: Adhesion properties, competition against enteropahtogens and modulation of IL-8 production. International Journal of Food Microbiology, vol. 125 (3), pp. 286-292, Jul. 2008.
PCT Written Opinion dated Dec. 16, 2011for PCT/IB2011/000561 filed on Mar. 17, 2011 in the name of Probiotical S.P.A.
PCT International Preliminary Report on Patentability dated Sep. 17, 2013 for PCT/IB2011/000561 filed on Mar. 17, 2011 in the name of Probiotical S.P.A.
Peran, L., et al., A comparative study of the preventative effects exerted by three probiotics, Bifidobacterium lactis, Lactobacillus casei and Lactobacillus acidophilus, in the TNBS model of rat colitis, J. Applied Microbiology 2007, 103: 836-844.
Zanoni, S., et al., Growth kinetics on oligo- and polysaccharides and promising features of three antioxidative potential probiotic strains, J. Applied Microbiology 2008, 105: 1266-1276.
Meei-yn, L., et al., Axtioxidative effect of intestinal bacteria Bifidobacterium longum ATCC 15708 and Lactobacillus acidophilus ATCC 4356, Digestive Diseases & Sciences 2000, 45: 1617-1622.
Lin, M., et al., Inhibition of lipid peroxidation by Lactobacillus acidophilus and Bifidobacterium longum , J. Agricultural & Food Chemistry 1999, 47: 3661-3664.
PCT International Search Report dated Mar. 29, 2012 for PCT/IB2012/000095 filed on Jan. 24, 2012 in the name of Probiotical S.p.A.
PCT Written Opinion dated Mar. 29, 2012 for PCT/IB2012/000095 filed on Jan. 24, 2012 in the name of Probiotical S.p.A.
PCT International Search Report dated Dec. 17, 2012 for PCT/IB2012/001745 filed on Sep. 10, 2012 in the name of Probiotical S.p.A.
Written Opinion dated Dec. 17, 2012 for PCT/IB2012/001745 filed on Sep. 10, 2012 in the name of Probiotical S.P.A.
International Search Report dated Dec. 3, 2012 for PCT/IB2012/001741 filed on Sep. 10, 2012 in the name of Giovanni Mogna.
Written Opinion dated Dec. 3, 2012 for PCT/IB2012/001741 filed on Sep. 10, 2012 in the name of Giovanni Mogna.
International Search Report dated Dec. 3, 2012 for International patent application PCT/IB2012/001848 filed on Sep. 21, 2012 in the name of Probiotical S.P.A.
International Written Opinion dated Dec. 3, 2012 for International patent application PCT/IB2012/001848 filed on Sep. 21, 2012 in the name of Probiotical S.P.A.
Search Report dated Nov. 11, 2011 for IT MI20110792 filed on May 9, 2011 in the name of Probiotical S.P.A.
Written Opinion dated Nov. 11, 2011 for IT MI20110792 filed on May 9, 2011 in the name of Probiotical S.P.A.
First Examination Report dated Apr. 28, 2014 for NZ IP No. 614002 filed on Aug. 6, 2013 in the name of Probiotical S.P.A.
Non-Final Office Action dated Jun. 5, 2014 for U.S. Appl. No. 14/005,821, filed Nov. 6, 2013.
A. Amaretti, et al. "Antioxidant properties of potentially probiotic bacteria: in vitro and in vivo activities", Applied Microbiology and Biotechnology. vol. 97 (2), 2013, pp. 809-817.

(56) References Cited

OTHER PUBLICATIONS

M. Candela, et al. "Interaction of probiotic *Lactobacillus* and *Bifidobacterium* strains with human intestinal epithelial cells: Adhesion properties, competition against enteropathogens and modulation of IL-8 production", International Journal of Food Microbiology, vol. 125 (3), pp. 286-292, Jul. 2008.

C P Champagne, et al: "The determination of viable counts in probiotic cultures microencapsulated by spray-coating", Food Microbiology, Academic Press Ltd, London, GB, vol. 27, No. 8, Dec. 1, 2010 (Dec. 1, 2010), pp. 1104-1111. Abstract Only.

A. Cheikhyoussef, et al. "Antimicrobial activity and partial characterization of bacteriocin-like inhibitory substances (BLIS) produced by *Bifidobacterium infantis* BCRC 14602", Food Control, Butterworth, London, GB, vol. 20 (6), pp. 553-559, Jun. 2009.

M.C. Collado, et al: "Probiotic Strains and Their Combination Inhibit In Vitro Adhesion of Pathogens to Pig Intestinal Mucosa", Current Microbiology, Springer-Verlag, NE, vol. 55, No. 3, Jul. 25, 2007 (Jul. 25, 2007), pp. 260-265. Abstract Only.

M. Del Piano, et al. "Evaluation of the intestinal colonization by microencapsulated probiotic bacteria in comparison with the same uncoated strains", Journal of Clinical Gastroenterology, vol. 44, pp. S42-S46, Sep. 2010.

Mario Del Piano, et al: "Is microencapsulation the future of probiotic preparations? The increased efficacy of gastro-protected probiotics", Gut Microbes Mar.-Apr. 2011 Lnkdpubmed: 21637030, vol. 2, No. 2, Mar. 2011 (Mar. 2011), pp. 120-123.

K.A. Eaton, et al: "Probiotic *Lactobacillus reuteri* Ameliorates Disease Due to Enterohemorrhagic *Escherichia coli* in Germfree Mice", Infection and Immunity, vol. 79, No. 1, Oct. 25, 2010 (Oct. 25, 2010), pp. 185-191.

M.F. Fernandez, et al: "Probiotic properties of human lactobacilli strains to be used in the gastrointestinal tract", Journal of Applied Microbiology, Oxford, GB, vol. 94, No. 3, Online Feb. 12, 2003, pp. 449-455.

FAO/WHO. Guidelines for the Evaluation of Probiotics in Food. Apr. 30-May 1, 2002, 11 pgs.

M. Gotteland, et al, "Systematic review: are probiotics useful in controlling gastric colonization by *Helicobacter pylori*?" Alimentary Pharmacology & Therapeutics, vol. 23, pp. 1077-1086, Apr. 15, 2006.

M Gueimonde, et al: "Adhesion and competitive inhibition and displacement of human enteropathogens by selected lactobacilli", Food Research International, Elsevier Applied Science, Barking, GB, vol. 39, No. 4, May 1, 2006 (May 1, 2006), pp. 467-471. Summary Citation.

H.Q. Huynh, et al: "N-Acetylcysteine, a Novel Treatment for *Helicobacter pylori* Infection", Digestive Diseases and Sciences, Kluwer Academic Publishers-Plenum Publishers, NE, vol. 49, No. 11-12, Nov. 1, 2004 (Nov. 1, 2004), pp. 1853-1861.

P Hütt, et al: "Antagonistic activity of probioitic lactobacilli and bifidobacteria aganst entero- and uropathogens", Journal of Applied Microbiology, vol. 100, No. 6, Jun. 2006 (Jun. 2006), pp. 1324-1332.

K.C. Johnson-Henry, et al: "*Lactobacillus rhamnosus* Strain GG Prevents Enterohemorrhagic *Escherichia coli* O157:H7-Induced Changes in Epithelial Barrier Function", Infection and Immunity, vol. 76, No. 4, Apr. 1, 2008 (Apr. 1, 2008), pp. 1340-1348.

J. Kim, et al. "Antimicrobial effect of *Bifidobacterium breve* and *Bifidobacterium infantis* against *Salmonella typhimurium* KCTC 1925 and *E.coli* O157:H7 ATCC 43895", Food Science and Biotechnology, Korean Society of Food Science and Technology, vol. 11 (1), pp. 89-92, Jan. 2002.

E. Likotrafiti, et al. "Molecular Identification and Anti-pathogenic Activities of Putative Probiotic Bacteria Isolated from Faeces of Healthy Elderly Individuals", Microbial Ecology in Health and Disease, 16, pp. 105-112 (2004).

Meei-Yn Lin, et al., "Axtioxidative effect of intestinal bacteria *Bifidobacterium longum* ATCC 15708 and *Lactobacillus acidophilus* ATCC 4356", Digestive Diseases & Sciences 2000, 45: 1617-1622.

Meei-Yn. Lin, et al., "Inhibition of lipid peroxidation by *Lactobacillus acidophilus* and *Bifidobacterium longum*", J. Agricultural & Food Chemistry 1999, 47: 3661-3664.

M.A. Losada, et al. "Towards a healthier diet for the colon: the influence of fructooligosaccharides and lactobacilli on intestinal health", Nutrition Research, vol. 22, Jan. 2002, pp. 71-84.

Hong Lu, et al: "New development in the mechanistic understanding of peptic ulcer diseases", Drug Discovery Today: Disease Mechanisms, Elsevier, vol. 3, No. 4, 2006, pp. 431-437.

F. Lutgendorff, et al., "Probiotics enhance pancreatic glutathione biosynthesis and reduce oxidative stress in experimental acute pancreatitis", Am. J. Physiol. Gastrointest. Liver Physiol., 2008, vol. 295; G1111-G1121.

M. Malecka, "Antioxidant properties of the unsaponifiable matter isolated from tomato seeds, oat grains and wheat germ oil" Food Chemistry, 2002, vol. 79, pp. 327-330.

A Marchese, et al.: "Effect of fosfomycin alone and in combination with N-acetylcysteine on *E. coli* biofilms", International Journal of Antimicrobial Agents, vol. 22, Oct. 1, 2003, Suppl. 2, (Oct. 1, 2003), pp. 95-100.

L.V. McFarland: "Meta-analysis of probiotics for the prevention of antibiotic associated diarrhea and the treatment of *Clostridium difficile* disease", The American Journal of Gastroenterology Apr. 2006 Lnkd-Pubmed:16635227, vol. 101, No. 4, Apr. 2006 (Apr. 2006), pp. 812-822.

M. Modesto, et al. "Resistance to freezing and freeze-drying storage processes of potential probiotic bifidobacteria", Annals of Microbiology, 54 (1), pp. 43-48 (2004).

L. Peran, et al., A comparative study of the preventative effects exerted by three probiotics, *Bifidobacterium lactis, Lactobacillus casei* and *Lactobacillus acidophilus*, in the TNBS model of rat colitis, J. Applied Microbiology 2007, 103: 836-844.

V. Rada, et al: "Susceptibility of bifidobacteria to lysozyme as a possible selection criterion for probiotic bifidobacterial strains", Biotechnology Letters, Springer Netherlands, Dordrecht, vol. 32, No. 3, Nov. 27, 2009 (Nov. 27, 2009), pp. 451-455. Abstract Only.

V. Rada, et al. "Susceptibility of bifidobacteria to nisin", Letters in Applied Microbiology, vol. 26, 1998, pp. 123-125.

C. Santini et al., "Characterization of probiotic strains: an application as feed additives in poultry against *Campylobacter jejuni*", Int J Food Microbiol., 2010, 141 Suppl 1:S98-108. Epub Apr. 8, 2010. Abstract Only.

S. Torriani, et al. "Differentiation of *Lactobacillus plantarum, L. pentosus*, and *L. paraplantarum* by recA Gene Sequence Analysis and Multiplex PCR Assay with recA Gene-Derived Primers", Appl. Environ. Microbiol. 2001. vol. 67 (8), pp. 3450-3454.

J. Walter, et al. "Detection and Identification of Gastrointestinal *Lactobacillus* Species by Using Denaturing Gradient Gel Electrophoresis and Species-Specific PCR Primers", Appl. Environ. Microbiol. 2000. vol. 66 (1), pp. 297-303.

Dan Yang Ying, et al: "Microencapsulated Lactobacillus rhamnosus GG Powders: Relationship of Powder Physical Properties to Probiotic Survival during Storage", Journal of Food Science, vol. 75, No. 9, Nov. 1, 2010 (Nov. 1, 2010), pp. E588-E595. Abstract Only.

S. Zanoni, et al., Growth kinetics on oligo- and polysaccharides and promising features of three antioxidative potential probiotic strains, J. Applied Microbiology 2008, 105: 1266-1276.

L. Zhang, et al., "Evaluation of Lactobacillus rhamnosus GG using an *Escherichia coli* K88 model of piglet diarrhoea: Effects on diarrhoea incidence, faecal microflora and immune responses", Veterinary Microbiology, Elsevier BV. NL, vol. 141, No. 1-2, Feb. 24, 2010, pp. 142-148. Epub Sep. 11, 2009. Abstract Only.

Office Action dated Jul. 15, 2014 for KZ Application No. 2013/1615.1 filed on Jan. 24, 2012 by Tagbergenova Alma Taishevna et al.

The EFSA Journal, "Opinion of the Scientific Panel on Additives and Products or Substances used in Animal Feed on the updating of the criteria used in the assessment of bacteria for resistance to antibiotics of human and veterinary importance", 2005, 223, pp. 1-12.

European Commission—Health & Consumer Protection Directorate-General, "Opinion of the Scientific Committee on Animal Nutrition

(56) References Cited

OTHER PUBLICATIONS on the Criteria for Assessing the Safety of Micro-Organisms Resistant to Antibiotics of Human Clinical and Veterinary Importance", 2002, pp. 1-20.
L. Ouoba, et al., "Resistance of potential probiotic lactic acid bacteria and bifidobacteria of African and European origin to antimicrobials: Determination and transferability of the resistance genes to other bacteria", International Journal of Food Microbiology, 2008, 121, 217-224.
D. Infante Pina, et al., "Prevalence and dietetic management of mild gastrointestinal disorders in milk-fed infants", World Journal of Gastroenterology, 2008, vol. 14, No. 2: 248-254.
First Office Action dated Nov. 4, 2014 for Chinese Patent Application No. 201280022854.9 filed on May 9, 2012 in the name of Probiotical S.P.A. (English + Chinese).
Non-Final Office Action dated Mar. 10, 2015 U.S. Appl. No. 13/982,225, filed Nov. 12, 2013 in the name of Giovanni Mogna.
Ronnqvist et al. (Lactobacillus fermentum Ess-1 with unique growth inhibition of vulvo-vaginal candidiasis pathogens. Journal of Medical Microbiology (2007), 56, 1500-1504).
Restriction Requirement dated Jan. 7, 2014 for U.S. Appl. No. 14/005,821, filed Nov. 6, 2013 in the name of Giovanni Mogna.
Non-Final Office Action dated Jun. 5, 2014 for U.S. Appl. No. 14/005,821, filed Nov. 6, 2013 in the name of Giovanni Mogna.
Lutgendorff, Fetal. Probiotics enhance pancreatic glutathione biosynthesis and reduce oxidative stress in experimental acute pancreatitis. Am. J. Physiol. Gastrointest. Liver Physiol. 2008. 295: G1111-G1121.
Malecka, M. Antioxidant properties of the unsaponifiable matter isolated from tomato seeds, oat grains and wheat germ oil. Food Chemistry. 2002. 79: 327-330.
Final Office Action dated Dec. 30, 2014 for U.S. Appl. No. 14/005,821, filed Nov. 6, 2013 in the name of Giovanni Mogna.
Restriction Requirement dated Feb. 20, 2015 for U.S. Appl. No. 14/117,003, filed Dec. 27, 2013 in the name of Giovanni Mogna.
Restriction Requirement dated Mar. 11, 2015 for U.S. Appl. No. 14/116,999, filed Dec. 20, 2013 in the name of Giovanni Mogna.
"7th Probiotics & Prebiotics—new food", Universita Urbaniana, Rome. Poster 66: "Effectiveness of the Two Microorganisms L. Fermentum LF15 and L. Plantarum LP01, Formulated in Slow Release Vaginal Tablets, in Women Affected by Bacterial Vaginosis (BV): A Pilot Study", pp. Cover-50, Jul. 2013.
"Sachet" Webpage from merriam-webster.com, Oct. 7, 2011, accessed via WayBackMachine.com. 1 page.
Al-Wahsh, I. et al. "Acute probiotic ingestion reduces gastrointestinal oxalate absorption in healthy subjects." Urological Research: A Journal of Clinical and Laboratory Investigation in Urolithiasis and Related Areas, vol. 40(3), pp. 191-196. Aug. 2011.
Castro-Leyva, V. et al. "Preserved Ex Vivo Inflammatory Status in Decidual Cells from Women with Preterm Labor and Subclinical Intrauterine Infection." Plos One, vol. 7 (8), e43605, pp. 1-6. Aug. 2012.
Del Piano, M. et al. Is microencapsulation the future of probiotic preparations? Gut Microbes, vol. 2 (2), 2011, pp. 120-123.
European Patent Office Communication pursuant to Article 94(3) EPC in relation to Application No. 12 780 278.3-1401. dated Jun. 6, 2015.
Fernandez, M.F. Probiotic properties of human lactobacilli strains to be used in the gastrointestinal tract. Journal of Applied Microbiology, vol. 94, 2003, pp. 449-455.
Grill et al. Canadian Journal of Microbiology. Oct. 2000, 46, pp. 878-884.
Grimoud, J. et al., "In vitro screening of probiotic lactic acid bacteria and prebiotic glucooligosaccharides to select effective synbiotics", Anaerobe, 16 (2010) 493-500.
Hoesl, C. E. et al. "The Probiotic Approach: An Alternative Treatment Option in Urology" European Urology, vol. 47, No. 3, pp. 288-296. Mar. 2005.

Hutt P. et al (2006) "Antagonistic activity of probioitic lactobacilli and bifidobacteria aganst entero- and uropathogens." Journal of Applied Microbiology. vol. 100. No. 6 pp. 1324-1332.
International Preliminary Report on Patentability for PCT/IB2012/001745 filed on Sep. 10, 2012 in the name of Probiotical North America Inc. dated Mar. 12, 2014.
International Search Report issued for International Application No. PCT/IB2014/000731 filed on May 14, 2014 in the name of Probiotical S.P.A. dated Jul. 25, 2014.
International Search Report issued for International Application No. PCT/IB2014/000739 filed on May 14, 2014 in the name of Probiotical S.P.A. dated Jul. 31, 2014.
International Search Report dated Dec. 17, 2012 for PCT/IB2012/001745 filed on Sep. 10, 2012 in the name of Probiotical S.P.A.
Klaver et al. "The Assumed assimilation of cholesterol by lactobacilli and Bifidobacterium bifidum is due to their bile salt-deconjugating activity" Appl Environ Microbiology, 1993, vol. 59, No. 4, pp. 1120-1124.
Lin, M.Y. et al. Antioxidative Effect of Intestinal Bacteria *Bifidobacterium longum* ATCC 15708 and *Lactobacillus acidophilus* ATCC 4356. Digestive Diseases and Sciences, vol. 45 (8), Aug. 2000, pp. 1617-1622.
Lu, et al: "New development in the mechanistic understanding of peptic ulcer diseases", Drug Discovery Today: Disease Mechanisms, Elsevier, vol. 3, No. 4, 2006, pp. 431-437.
Milani, C. et al., "Comparative Genomics of *Bifidobacterium animalis* subsp. *lactis* Reveals a Strict Monophyletic Bifidobacterial Taxon", Applied and Environmental Microbiology, 79 (14), 2013, 4304-4315.
Mogna, L. et al. "Assessment of the in vitro inhibitory activity of specific probiotic bacteria against different *Escherichia coli* strains." Journal of Clinical Gastroenterology, vol. 46, Supp. 1, pp. S29-S32. Oct. 2012.
Non-Final Office Action dated Jun. 16, 2015 for U.S. Appl. No. 14/116,999, filed Dec. 20, 2013 in the name of Giovanni Mogna. 29 pages.
Pascual, L. et al. "Vaginal Colonization and Activity of the Probiotic Bacterium *Lactobacillus fermentum* L23 in a Murine Model of Vaginal Tract Infection", Journal of Medical Microbiology, vol. 59, No. 3, pp. 360-364, Nov. 2009.
PCT International Preliminary Report on Patentability dated Jul. 30, 2013 for PCT/IB2012/000095 filed on Jan. 24, 2012 in the name of Probiotical S.p.A.
PCT International Preliminary Report on Patentability dated Nov. 12, 2013 for PCT/IB2012/000907 filed on May 9, 2012 in the name of Probiotical S.P.A.
PCT International Search Report issued for PCT/IB2012/001745 filed on Sep. 10, 2012 in the name of Probiotical S.P.A. dated Dec. 17, 2012.
PCT International Search Report issued for PCT/IB2012/001848 filed on Sep. 21, 2012 in the name of Giovanni Mogna. dated Dec. 3, 2012.
PCT International Search Report dated Dec. 16, 2011for PCT/IB2011/000561 filed on Mar. 17, 2011 in the name of Probiotical S.P.A.
PCT International Search Report dated Dec. 3, 2012 for PCT/IB2012/001741 filed on Sep. 10, 2012 in the name of Giovanni Mogna.
PCT Written Opinion issued for International Application No. PCT/IB2014/000731 filed on May 14, 2014 in the name of Probiotical S.P.A. dated Jul. 25, 2014.
PCT Written Opinion issued for International Application No. PCT/IB2014/000739 filed on May 14, 2014 in the name of Probiotical S.P.A. dated Jul. 31, 2014.
PCT Written Opinion issued for PCT/IB2012/001745 filed on Sep. 10, 2012 in the name of Probiotical S.P.A. dated Dec. 17, 2012.
PCT Written Opinion issued for PCT/IB2012/001848 filed on Sep. 21, 2012 in the name of Giovanni Mogna. dated Dec. 3, 2012.
Restriction Requirement issued for U.S. Appl. No. 13/982,255, filed Nov. 12, 2013 in the name of Giovanni Mogna. dated Oct. 17, 2014.
Restriction Requirement issued for U.S. Appl. No. 14/344,021, filed May 9, 2014 in the name of Giovanni Mogna. dated Aug. 14, 2015.

(56) References Cited

OTHER PUBLICATIONS

Restriction Requirement dated Jan. 7, 2014 for U.S. Appl. No. 14/005,821, filed Nov. 6, 2013.
S. Keersmaecker et al. "Strong antimicrobial activity of Lactobacillus rhamnosus GG against *Salmonella typhimurium* is due to accumulation of lactic acid" Federation of European Microbiological Societies Microbiology Letters 259. (2006) 89-96.
Saggioro, A. "Probiotics in the Treatment of Irritable Bowel Syndrome." Journal of Clinical Gastroenterology, vol. 38(6), pp. S104-S106. Jul. 2004.
Strus, M. et al. "Studies on the Effects of Pro Biotic *Lactobacillus* Mixture Given Orally on Vaginal and Rectal Colonization and on Parameters of Vaginal Health in Women with Intermediate Vaginal Flora" Eurpoean Journal of Obstetrics Gynecology and Reproductive Biology, vol. 163, No. 2 pp. 210-215. Aug. 2012.
Vicariotto, F. et al: "65: Effectiveness of an Association of a Cranberry Dried Extract, D-Mannose and the Three Microorganisms L. Plantarum Lp01, L. Paracasei, Lpc09 and S. Thermophilus St10 In Women Affected by Cystitis: A Pilot Study", 7th Probiotics & Prebiotics New Foods, pp. 1-52, Jul. 2013.
Alam, M. et al. "Development and Evaluation of Acid-buffering Bioadhesive Vaginal Tablet for Mixed Vaginal Infections" AAPS PharmSciTech 2007; vol. 8, No. 4, Article 109. pp. E1-E8.
Bordoni, A. et al. "Cholesterol-lowering probiotics: in vitro selection and in vivo testing of bifidobacteria" Applied Microbiology and Biotechnology. Sep. 2013. vol. 97, No. 18 pp. 8273-8281.
Briczinski, E. et al. "Strain-Specific Genotyping of *Bifidobacterium animalis* subsp. *lactis* by Using Single-Nucleotide Polymorphisms, Insertions, and Deletions" Applied and Environmental Microbiology. Dec. 2009. vol. 75, No. 23, pp. 7501-7508.
Chilean First Examination report dated Mar. 9, 2016 for Chilean application No. 2013-002148 filed on Jul. 26, 2013 in the name of Probiotical S.P.A., 21 pgs. (Spanish with English translation.).
European Patent Office Communication pursuant to Article 94(3) EPC in relation to Application No. 12 780 278.3-1401. dated Jun. 12, 2015 4 pages.
First Office Action for Chinese Patent Application No. 201280015994.3 dated Mar. 25, 2016. 23 pages. (Chinese original + English translation).
Guo, X. "Basics and Application of Probiotics" Science and Technology Press, 1st Version, Oct. 2002. 2 pages (Chinese Original + English Translation).
http://intranet.comunidadandina.org/Documentos/Gacetas/Gace722. PDF Breach Action Filed by the General Secretary of the Andean Community Against the Republic of Peru, Process 89-AI-2000 (Gaceta Oficial, del Acuerdo de Cartagena, Sumario, Tribunal de Justicia de la Comunidad Andina), Ano XVIII, Numero 722, Lima, Oct. 12, 2001, 44 pgs. Spanish with English Abstract.
http://www.ub.es/legmh/capitols/sunyenegre.pdf Dr. Jose Ma Sune Negre, New Galenic Formulations to Forms of Administration (Nuevas Aportaciones Galenicas a las Formas de Administracion. En: Curos de formacion continuada para farmaceuticos de hospital. Fundacion Promocion Medica. Barcelona, 2002, 3, pp. 27-65), 3.2. 27 pgs. Spanish with English Abstract.
Italian Search Report and Written Opinion dated Nov. 11, 2011 for MI20110792 filed on May 9, 2012 in the name of Probiotical S.p.A. 9 pages.
Japanese Patent Office Official Action for Japanese Patent Application No. 2013-550962. dated Dec. 1, 2015. 10 pages. (Japanese original + English translation).
McFarland, L.V. et al. Meta-analysis of Probiotics for the Prevention of Antibiotic Associated Diarrhea and the Treatment of *Clostridium difficile* Disease. American Journal of Gastroenterology, vol. 101, 2006, pp. 812-822.
Mei, X. et al. "Manual of New Drug and Special Drug" Technology Press, 2nd Version, Jan. 2001. 2 pages (Chinese Original + English Translation).
Office Action for Russian Patent Application No. 2013137656/15(056766) filed Jan. 24, 2012 on behalf of Probiotical S.P.A. dated Mar. 18, 2016. 10 pages (Russian original + English translation).

Opposition filed to Application No. SP-2013-12844. 14 pages. Spanish original with English Translation; Date of Notification: Nov. 17, 2015.
Opposition to Ecuadorian Patent Application SP-2013-13082 on behalf of Alafar. 14 pages (Spanish original + English translation).
Ouwehand, A. et al. "Probiotics: an Overview of beneficial effects" Antonie van Leeuwenhoek. 2002, vol. 82; pp. 279-289.
Pascual, L. et al. "Vaginal Colonization and Activity of the Probiotic Bacterium *Lactobacillus fermentum* L23 in a Murine Model of Vaginal Tract Infection", Journal of Medical Microbiology, vol. 59, No. 3, pp. 360-364, 2010.
PCT International Preliminary Report on Patentability issued for International Application No. PCT/IB2014/000739 filed on May 14, 2014 in the name of Probiotical S.P.A. dated Nov. 26, 2015. 14 pages.
Puccio, G. et al. "Clinical evaluation of a new starter formula for infants containing live *Bifidobacterium longum* BL999 and prebiotics" Nutrition 2007 vol. 23; pp. 1-8.
Wikipedia "Pharmaceutical Drug" Updated Apr. 15, 2016. Downloaded from the internet Apr. 21, 2016. 11 pages.
Wikipedia, "Strain (biology)" https://en.wikipedia.org/wiki/Strain_(biology) Retrieved on Nov. 3, 2015. 2 pgs.
Notice of Allowance for U.S. Appl. No. 13/982,255, filed Nov. 12, 2013 on behalf of Giovanni Mogna. dated Jan. 22, 2016. 10 pages.
Notice of Allowance for U.S. Appl. No. 13/982,255, filed Nov. 12, 2013 on behalf of Giovanni Mogna. dated Jun. 15, 2016. 11 pages.
Notice of Allowance for U.S. Appl. No. 13/982,255, filed Nov. 12, 2013 on behalf of Giovanni Mogna. dated Jul. 27, 2016. 9 pages.
Final Office Action for U.S. Appl. No. 14/117,003, filed Dec. 27, 2013 on behalf of Giovanni Mogna. dated Jun. 2, 2016. 11 pages.
Non-Final Office Action for U.S. Appl. No. 14/116,999, filed Dec. 20, 2013 on behalf of Giovanni Mogna. dated Mar. 14, 2016. 25 pages.
Restriction Requirement for U.S. Appl. No. 14/344,047, filed Jul. 28, 2014 on behalf of Giovanni Mogna. dated Feb. 19, 2016. 8 pages.
Non-Final Office Action for U.S. Appl. No. 14/344,021, filed May 9, 2014 on behalf of Giovanni Mogna. dated Apr. 18, 2016. 29 pages.
Restriction Requirement for U.S. Appl. No. 14/891,306, filed Nov. 13, 2015 on behalf of Giovanni Mogna. dated Apr. 13, 2016. 7 pages.
Turroni, S, et al. "Oxalate consumption by lactobacilli: evaluation of oxalyl-CoA decarboxylase and formyl-CoA transferase activity in *Lactobacillus acidophilus*" Journal of Applied Microbiology, 2007, 103, pp. 1600-1609.
7th Probiotics, Prebiotics & New Foods Proceedings and Abstracts, Retrieved from Internet, [Retrieved on Sep. 2013] URL:<http://www.probioticsprebiotics-newfood.com/pdf/7thPmbioticsPrebioticsNewfood.pdf> Sep. 2013, 206 pages.
Aloisio I., et al., "Characterization of *Bifidobacterium* spp. Strains for the Treatment of Enteric Disorders in Newborns," Applied Microbiology and Biotechnology, Dec. 2012, vol. 96 (6), 19 pages.
Antao E.M., et al., "The Chicken as a Natural Model for Extraintestinal Infections caused by Avian Pathogenic *Escherichia coli* (APEC)," Microbial Pathogenesis, Nov.-Dec. 2008, vol. 45 (5-6), 9 pages.
Anukam K.C., et al., "Lactobacillus Plantarum and Lactobacillus Fermentum with Probiotic Potentials Isolated from the Vagina of Healthy Nigerian Women," Research Journal of Microbiology, 2007, vol. 2 (1), 8 pages.
Barber A.E., et al., "Strengths and Limitations of Model Systems for the Study of Urinary Tract Infections and Related Pathologies," Microbiology and Molecular Biology Reviews, Jun. 2016, vol. 80 (2), 18 pages.
Bespalov V.G., et al., "Biologically active food supplements," Kafedra, 2000, 12 pages.
Best E.L., et al., "Models for the Study of Clostridium Difficile Infection," Gut Microbes, Mar.-Apr. 2012, vol. 3 (2), 23 pages.
Broadbent J.R., et al., "Biochemistry, Genetics, and Applications of Exopolysaccharide Production in *Streptococcus thermophiles*: A Review," Journal of Dairy Science, Feb. 2003, vol. 86 (2), 17 pages.

(56) References Cited

OTHER PUBLICATIONS

Busch N.A., et al., "A Model of Infected Burn Wounds Using *Escherichia coli* O18:K1:H7 for the Study of Gram-Negative Bacteremia and Sepsis," Infection and Immunity, Jun. 2000, vol. 68 (6), 3 pages.
Candela M., et al., "High Taxonomic Level Fingerprint of the Human Intestinal Microbiota by Ligase Detection Reaction—Universal Array Approach," BMC Microbiology, Apr. 2010, vol. 10 (116), 17 pages.
Champagne C.P., et al., "The Determination of Viable Counts in Probiotic Cultures Microencapsulated by Spray-Coating," Food Microbiology, Dec. 2010, vol. 27 (8), 1 page.
Chen H.L., et al., "Probiotic Lactobacillus casei Expressing Human Lactoferrin Elevates Antibacterial Activity in the Gastrointestinal Tract," Biometals, Jun. 2010, vol. 23 (3), 12 pages.
Cremonini F., et al., "Effect of Different Probiotic Preparation son Anti-Helicobacter pylori Therapy-Related Side Effects: A Parallel Group, Triple Blind, Placebo-Controlled Study," American Journal of Gastroenterology, 2002, vol. 97 (11), 7 pages.
Darouiche R.O., et al., "Bacterial Interference for Prevention of Urinary Tract Infection: A Prospective, Randomized, Placebo-controlled, Double-blind Pilot Trial," Clinical Infectious Diseases : An Official Publication of the Infectious Diseases Society of America, Nov. 2005, vol. 41 (10), 4 pages.
Decision to Grant a Patent for Invention issued for Russian application No. 2013148474 filed on May 9, 2012, dated May 19, 2017, 11 pages (English Translation and Russian Original).
Decision to Grant dated May 31, 2017 for Russian Patent Application No. 2013148476/15 filed on May 9, 2012 on behalf of Probiotical S.P.A, 15 pages. (Russian Original + 2 pages of English Translation).
Decision to Grant dated Sep. 2, 2016 for Russian Patent Application No. 2014110640/05 filed on Sep. 21, 2012 on behalf of Probiotical S.P.A., 9 pages.
Del Piano M., et al., "Correlation Between Chronic Treatment with Proton Pump Inhibitors (PPIs) and Bacterial Overgrowth in the Stomach: Any Possible Beneficial Role for Selected Lactobacilli?," Journal of clinical gastroenterology, Nov. 2014, vol. 48 Suppl 1, 7 pages.
DeNol, retrieved on Mar. 39, 2016, from the Internet: URL:www.rlsnet.ru/tn_index_id_6426.html, 2009, 5 pages.
Douillard F.P., et al., "Comparative Genomic and Functional Analysis of 100 Lactobacillus Rhamnosus Strains and their Comparison with Strain GG," PLOS Genetics, Aug. 2013, vol. 9 (8), 15 pages.
Federici F., et al., "Characterization and HeterologousExpression of the Oxalyl Coenzyme A Decarboxylase Gene from Bifidobacterium lactis," Applied and EnvironmentalMicrobiology, Sep. 2004, vol. 70 (9), 8 pages.
Final Office Action for U.S. Appl. No. 13/982,255, filed Nov. 12, 2013 on behalf of Giovanni Mogna. dated Sep. 17, 2015, 15 pages.
Final Office Action for U.S. Appl. No. 14/113,211, filed Nov. 26, 2016 on behalf of Giovanni Mogna. dated Nov. 22, 2016, 12 pages.
Final Office Action for U.S. Appl. No. 14/116,999, filed Dec. 20, 2013 on behalf of Giovanni Mogna. dated Dec. 9, 2016, 28 pages.
Final Office Action for U.S. Appl. No. 14/344,021, filed May 9, 2014 on behalf of Giovanni Mogna. dated Jan. 31, 2017, 19 pages.
Final Office Action for U.S. Appl. No. 14/344,047, filed Jul. 28, 2014 on behalf of Giovanni Mogna. dated Aug. 4, 2017, 29 pages.
Final Office Action for U.S. Appl. No. 14/346,941, filed Mar. 24, 2014 on behalf of Probiotical North America Inc. dated Jan. 22, 2018. 14 pages.
Final Office Action for U.S. Appl. No. 14/891,306, filed Nov. 13, 2015 on behalf of Probiotical S.P.A. dated Jan. 18, 2018. 41 pages.
Final Office Action for U.S. Appl. No. 14/891,321, filed Nov. 13, 2015 on behalf of Probiotical S.P.A. dated Apr. 25, 2018. 8 pages.
Final Office Action for U.S. Appl. No. 15/265,706, filed Sep. 14, 2016 on behalf of Probiotical S.P.A. dated Feb. 2, 2018. 34 pages.
Germond J.E., et al., "Evolution of the Bacterial Species *Lactobacillus delbrueckii*: a Partial Genomic Study with Reflections on Prokaryotic Concept," Molecular Biology and Evolution, Jan. 2003, vol. 20 (1), 12 pages.
Guardamagna O., et al., "Bifidobacteria Supplementation: Effects on Plasma Lipid Profiles in Dyslipidemic Children," Nutrition, Jul.-Aug. 2014, vol. 30 (7-8), 6 pages.
Guonong et al., China; Light Industry Press, 1st Edition in 2009, pp. 363, Publication Date: Aug. 31, 2009, 2 pages (Chinese original + English excerpt).
Gurbuz A.K., et al., "Effect of N-Acetyl Cysteine on Helicobacter Pylori," Souther Medical Journal, Nov. 2005, vol. 98 (11), 4 pages.
Hamilton-Miller J.M., et al., "The Role of Probiotics in the Treatment and Prevention of Helicobacter Pylori Infection," International Journal of Antimicrobial Agents, Oct. 2003, vol. 22 (4), 7 pages.
Hemert S.V., et al., "Influence of the Multispecies Probiotic Ecologic® Barrier on Parameters of Intestinal Barrier Function," Food and Nutrition Sciences, Sep. 2014, vol. 5 (18), 8 pages.
International Search Report for Application No. PCT/IB2012/000779, dated Jul. 19, 2012, 5 pages.
Japanese Patent Office Official Action for Japanese Patent Application No. 2013558517, dated Mar. 3, 2015, 4 pages. (Japanese original + English translation).
Japanese Patent Office Official Action for Japanese Patent Application No. 2014509849, dated Apr. 26, 2016, 9 pages. (Japanese original + English translation).
Japanese Patent Office Official Action for Japanese Patent Application No. 2014529081, dated May 31, 2016, 8 pages. (Japanese original + English translation).
Japanese Patent Office Official Action Summary for Japanese Patent Application No. 2014509850 filed on behalf of Probiotical S.P.A., dated Feb. 16, 2016, 5 pages. (Japanese original + English translation).
Kanamori Y., et al., "Parenteral and Enteral Nutrition," 2010, vol. 25 (4), 1 page.
Karamanolis G., et al., "A Glass of Water Immediately Increases Gastric pH in Healthy Subjects," Digestive Diseases and Sciences, Dec. 2008, vol. 53 (12), 5 pages.
Khavkin A.I., et al., "Modern Principles of Ulcer Disease," retrieved on Mar. 29, 2016, from the internet: URL: www.lvrach.ru/2005/02/4532114/, 6 pages (Russian original + English translation of relevant parts).
Kim H.S., et al., "In vitro Antioxidative Properties of Lactobacilli," Asian-Australasian Journal of Animal Sciences, 2006, vol. 19 (2), 5 pages.
Kizerwetter-Swida M., et al., "Selection of Potentially Probiotic Lactobacillus Strains Towards Their Inhibitory Activity Against Poultry Enteropathogenic Bacteria," Polish Journal of Microbiology, 2005, vol. 54 (4), 8 pages.
Krosnynk I.I., et al., "Pharmaceutical Technology: Technology of Dosage Forms: A Textbook for University Students," Academia Editorial Center, 2006, 3 pages (Russian Original + English Translation of Relevant Parts).
Lieske J.C., et al., "Use of a Probiotic to Decrease Enteric Hyperoxaluria," Kidney International, Sep. 2005, vol. 68 (3), 6 pages.
Liu J.R., et al., "Antioxidative Activities of Kefir," Asian-Australasian Journal of Animal Sciences, 2005, vol. 18 (4), 8 pages.
Masashi Okamura, "Youkei no Tomo," 2008, vol. 558, 1 page.
Mathews H.M., et al., "Sodium Bicarbonate as a Single Dose Antacid in Obstetric Anaesthesia," Anaesthesia, Jul. 1989, vol. 44 (7), 2 pages.
Moen S.T., et al., "Testing the Efficacy and Toxicity of Adenylyl Cyclase Inhibitors Against Enteric Pathogens Using in Vitro and in Vivo Models of Infection," Infection and Immunity, Apr. 2010, vol. 78 (4), 10 pages.
Mogna, L., et al., "Screening of Different Probiotic Strains for Their In Vitro Ability to Metabolise Oxalates: Any Prospective Use in Humans?" Journal of Clinical Gastroenterology, 2014, vol. 48, S91-S95). 5 pages.
Mogna L., et al., "In Vitro Inhibition of Klebsiella Pneumoniae by *Lactobacillus delbrueckii* Subsp. *delbrueckii* LDD01 (DSM 22106): An Innovative Strategy to Possibly Counteract Such Infections in Humans?," Journal of Clinical Gastroenterology, Nov.-Dec. 2016, vol. 50 (Supp 2), 4 pages.

(56) References Cited

OTHER PUBLICATIONS

Non-Final Office Action for U.S. Appl. No. 13/982,255, filed Nov. 12, 2013 on behalf of Giovanni Mogna. dated Mar. 10, 2015, 10 pages.
Non-Final Office Action for U.S. Appl. No. 14/113,211, filed Nov. 26, 2013 on behalf of Giovanni Mogna. dated Dec. 7, 2017. 36 pages.
Non-Final Office Action for U.S. Appl. No. 14/113,211, filed Nov. 26, 2013 on behalf of Giovanni Mogna. dated Apr. 22, 2015, 13 pages.
Non-Final Office Action for U.S. Appl. No. 14/113,211, filed Nov. 26, 2013 on behalf of Giovanni Mogna. dated Jan. 22, 2016, 13 pages.
Non-Final Office Action for U.S. Appl. No. 14/116,999, filed Dec. 20, 2013 on behalf of Giovanni Mogna. dated Jan. 5, 2018. 26 pages.
Non-Final Office Action for U.S. Appl. No. 14/117,003, filed Dec. 27, 2013 on behalf of Giovanni Mogna. dated Oct. 14, 2015, 18 pages.
Non-Final Office Action for U.S. Appl. No. 14/344,021, filed May 9, 2014 on behalf of Giovanni Mogna. dated Jul. 24, 2017, 18 pages.
Non-Final Office Action for U.S. Appl. No. 14/344,047, filed Jul. 28, 2014 on behalf of Giovanni Mogna. dated Oct. 13, 2016, 27 pages.
Non-Final Office Action for U.S. Appl. No. 14/346,941, filed Mar. 24, 2014 on behalf of Probiotical North America Inc dated Apr. 19, 2017, 14 pages.
Non-Final Office Action for U.S. Appl. No. 14/891,306, filed Nov. 13, 2015 on behalf of Probiotical S.P.A. dated Nov. 22, 2016, 37 pages.
Non-Final Office Action for U.S. Appl. No. 14/891,321, filed Nov. 13, 2015 on behalf of Probiotical S.P.A. dated Sep. 6, 2017, 14 pages.
Non-Final Office Action for U.S. Appl. No. 15/265,706, filed Sep. 14, 2016 on behalf of Probiotical S.P.A. dated Jul. 11, 2017, 14 pages.
Notice of Allowance for U.S. Appl. No. 14/117,003, filed Dec. 27, 2013 on behalf of Giovanni Mogna. dated Jul. 6, 2017, 10 pages.
Notice of Allowance for U.S. Appl. No. 14/117,003, filed Dec. 27, 2013 on behalf of Giovanni Mogna. dated Nov. 9, 2016, 7 pages.
Notice of Allowance for U.S. Appl. No. 14/117,003, filed Dec. 27, 2013 on behalf of Giovanni Mogna. dated Nov. 22, 2016, 8 pages.
Notice of Allowance for U.S. Appl. No. 14/344,021, filed May 9, 2014 on behalf of Giovanni Mogna. dated Dec. 15, 2017. 7 pages.
Notice of Allowance for U.S. Appl. No. 14/344,021, filed May 9, 2014 on behalf of Giovanni Mogna. dated Mar. 27, 2018. 9 pages.
Notification of the Second Office Action for Chinese Patent Application No. 201280034204.6 filed on behalf of Probiotical S.P.A. dated Oct. 21, 2016, 17 pages. (Chinese Original + English translation).
Office Action for Japanese Patent Application No. JP201651345, dated Jan. 16, 2018, 7 pages. (English Translation + Japanese Original).
Office Action for Russian Patent Application No. 2014107771/10(012274) filed on behalf of Probiotical S.P.A. dated Jun. 2, 2016, 8 pages. (Russian original + English translation).
Office Action Inquiry for Russian Patent Application No. 2013144267 filed on Mar. 17, 2011 on behalf of Probiotical S.P.A. dated Mar. 12, 2015, 5 pages. (English Translation).
Office Action dated Feb. 13, 2017 for Chinese Patent Application No. 201280022854.9 filed on May 9, 2012 in the name of Probiotical S.P.A., 12 pages. (English + Chinese).
Office Action dated Feb. 15, 2016 for Chinese Patent Application No. 201180070870.0, 15 pages. (Chinese original + English translation).
Official Action for Russian Patent Application No. 2013151611 filed Apr. 18, 2012 on behalf of Giovanni Mogna, 12 pages. (Russian original + English translation).
Qingbin et al., Science Press, 1st Edition, Jun. 2012, 7 pages. (Chinese Original + English Excerpt).
Restriction Requirement for U.S. Appl. No. 14/113,211, filed Nov. 26, 2013 on behalf of Giovanni Mogna. dated Sep. 5, 2014, 9 pages.
Restriction Requirement for U.S. Appl. No. 14/346,941, filed Mar. 24, 2014 on behalf of Probiotical North America Inc dated Nov. 16, 2016, 8 pages.
Restriction Requirement for U.S. Appl. No. 14/891,321, filed Nov. 13, 2015 on behalf of Probiotical S.P.A. dated Jun. 16, 2017, 6 pages.
Ritchie J.M. "Animal Models of Enterohemorrhagic *Escherichia coli* Infection," Microbiology Spectrum, Aug. 15, 2014, vol. 2(4), 13 pages, EHEC-0022-2013.
Scardovi V., et al., "Multiple Electrophoretic Forms of Transaldolase and 6-Phosphogluconic Dehydrogenase and Their Relationships to the Taxonomy and Ecology of the Bifidobacteria," International Journal of Systematic and Evolutionary Microbiology, Original Papers Relating to Systematic Bacteriology, vol. 29 (4), Oct. 1979, 16 pages.
Sgouras D.N., et al., "Lactobacillus Johnsonii La1 Attenuates Helicobacter Pylori-associated Gastritis and Reduces Levels of Proinflammatory Chemokines in C57bl/6 Mice," Clinical and Diagnostic Laboratory Immunology, Edited by U. Gallo, L. Santamaria., Dec. 2005, vol. 12 (12), 10 pages.
Shigeru Kamiya, "Igaku No Ayumi," Journal of Clinical and Experimental Medicine, 2003, vol. 207 (10), 7 pages.
Shim Y.H., et al., "Antimicrobial Activity of Lactobacillus Strains Against Uropathogens," Pediatrics International, Oct. 2016, vol. 58 (10), 5 pages.
Shu Q., et al., "Immune Protection Mediated by the Probiotic Lactobacillus Rhamnosus HN001 (DR20) Against *Escherichia coli* O157:H7 Infection in Mice," FEMS Immunology and Medical Microbiology, Sep. 2002, vol. 34 (1), 6 pages.
Terris M.K., et al., "Dietary Supplementation with Cranberry Concentrate Tablets May Increase the Risk of Nephrolithiasis," Urology, Jan. 2001, vol. 57 (1), 4 pages.
Third Office Action for Chinese Patent Application No. 201280022854.9, dated May 17, 2016. 12 pages. (Chinese original + English translation).
Tsai C.C., et al., "Three Lactobacillus Strains From Healthy Infant Stool Inhibit Enterotoxigenic *Escherichia coli* Grown in Vitro," Anaerobe, Apr. 2008, vol. 14 (2), 7 pages.
Vasiljevic T., et al., "Probiotics—From Metchnikoff to bioactives," International Dairy Journal, Jul. 2008, vol. 18 (7), 15 pages.
Ventura M. et al., "Identification and Tracing of *Bifidobacterium* Species by Use of Enterobacterial Repetitive Intergenic Consensus Sequences," Applied and Environmental Microbiology, vol. 69 (7), Jul. 2003, 6 pages.
Vicariotto F, "Effectiveness of an Association of a Cranberry Dry Extract, D-Mannose, and the two Microorganisms Lactobacillus Plantarum LP01 and Lactobacillus Paracasei LPC09 in Women Affected by Cystitis: A Pilot Study," Clinical Gastroenterology, Nov.-Dec. 2014, vol. 48 Suppl 1, 6 pages.
Wang K.Y., et al., "Effects of Ingesting Lactobacillus- and Bifidobacterium-Containing Yogurt in Subjects With Colonized Helicobacter Pylori," American Journal of Clinical Nutrition, Sep. 2004, vol. 80 (3), 5 pages.
Wikipedia "Colony-Forming Unit", Downloaded from the internet Apr. 13, 2017. http://en.wikipedia.org/wiki/Colony-forming unit, 1 page.
Wiktionary "Bifidogenic" Last modified Jul. 19, 2014, Retrieved from the internet on Apr. 13, 2017, from http://en.wiktionary.org/wiki/bifidogenic, 1 page.
Wiktionary "Cluster—definition" retrieved from the internet on Apr. 27, 2017 from http://web.archive.org/web/20100214060846/https://en.wiktionary.org/wiki/cluster, 4 pages.
Written Opinion for Application No. PCT/IB2012/000779, dated Jul. 19, 2012, 5 pages.
Ying D.Y., et al., "Microencapsulated Lactobacillus Rhamnosus GG Powders: Relationship of Powder Physical Properties to Probiotic Survival During Storage," Journal of Food Science, Nov. 2010, vol. 75 (9), 1 page.

(56) References Cited

OTHER PUBLICATIONS

Yoon Y., et al., "Occurrence of Glutathione Sulphydryl (GSH) and Antioxidant Activities in Probiotic *Lactobacillus* Spp," Asian-Australasian Journal of Animal Sciences, 2004, vol. 17 (11), 5 pages.
Zarate et al., "Protective Effect of Vaginal Lactobacillus Paracasei CRL 1289 Against Urogenital Infection Produced by *Staphylococcus aureus* in a Mouse Animal Model," Infectious Diseases in Obstetrics and Gynecology, Mar. 2007, 6 pages.
Advisory Action U.S. Appl. No. 14/344,047, filed Jul. 28, 2014 on behalf of Giovanni Mogna. dated Nov. 28, 2017. 13 pages.
Baluka et al., "PCR-Based Detection of Genes Responsible for Oxalate Detoxification in Probiotic Microorganisms," Annual Meeting of the Illinois State Academy of Sciences, 2008 Retrieved from the Internet: [https://www.eiu.edu/biology/posters/2008-11.pdf], 1 page.
Chinese Patent Office First Office Action for Chinese Patent Application No. 201480027970.9. dated Jul. 3, 2018. 12 pages. (Chinese Original + English translation).
Chinese Search Report for Chinese Application No. 201480027970.9 filed May 14, 2014 on behalf of Probiotical S.P.A. dated Jun. 21, 2018. 7 pages. (Chinese Original + English Translation).
Decision of Rejection for CN201280022854 filed on behalf of Probiotical S.P.A. on Nov. 11, 2013. dated Sep. 8, 2017. (Chinese Original + English translation). 18 pages.
Final Office Action for U.S. Appl. No. 14/113,211, filed Nov. 26, 2013, on behalf of Hoffmann-Eitle SRL. dated Sep. 28, 2018. 23 pgs.
Fourth Office Action for Chinese Patent Application No. 201280015994.3 filed on behalf of Probiotical S.P.A. dated May 22, 2018. 20 pages. (English Translation + Chinese Original).
Giglione, E., et al. "The Association of Bifidobacterium breve BR03 and B632 is Effective to Prevent Colics in Bottle-fed Infants", Journal of Clinical Gastroenterology, vol. 50 (2), S164-S167, (Nov. 2016). 4 pages.
International Preliminary Report on Patentability for International Application No. PCT/IB2014/000731 filed May 14, 2014 on behalf of Probiotical S.P.A. dated Nov. 17, 2015. 11 pages.
Jackson, S.A. et al., "Improving End-User Trust in the Quality of Commercial Probiotic Products", Frontiers in Microbiology, Apr. 2019, vol. 10, Article 739, 15 pages. http://www.frontiersin.org.
Klemenak, M., et al., "Administration of Bifidobacterium breve Decreases the Production of TNF-a in Children with Celiac Disease," Dig Dis Sci. 60(11):3386-92, 2015. 7 pages.
Lai, et al., "Lansoprazole for the Prevention of Recurrences of Ulcer Complications From Long-Term Low-Dose Aspirin Use", N Engl J Med. 346 (26) 2002: 2033-2038.
Lee, Y.K., et al., "Handbook of Probiotics and Prebiotics", Second Edition (2009), John Wiley & Sons, Inc. pp. 4, 5 and 24. 5 pages of English copy.
Macfarlane S., et al., "Review Article: Prebiotics in the Gastrointestinal Tract," Alimentary Pharmacology & Therapeutics, Sep. 2006, vol. 24 (5), pp. 701-714. 14 pages.
McFarland, et al. "Strain-Specificity and Disease-Specificity of Probiotic Efficacy: A Systematic Review and Meta-Analysis", Frontiers in Medicine, vol. 5, Article 124, (May 2018), 14 pages.
McFarland L.V., "Meta-analysis of Probiotics for the Prevention of Antibiotic Associated Diarrhea and the Treatment of Clostridium Difficile Disease," The American Journal of Gastroenterology, Apr. 2006, vol. 101 (4), pp. 812-822. 11 pages.
Mogna, et al. "Capability of the Two Microorganisms Bifidobacterium breve B632 and Bifidobacterium breve BR03 to Colonize the Intestinal Microbiota of Children", Journal of Clinical Gastroenterology, vol. 48 (1), S37-S39, (Nov. 2014). 3 pages.
Non-Final Office Action for U.S. Appl. No. 14/113,211, filed Nov. 26, 2013 on behalf of Hoffmann-Eitle SRL. dated May 29, 2019. 29 pages.
Non-Final Office Action for U.S. Appl. No. 15/265,706, filed Sep. 14, 2016 on behalf of Probiotical S.P.A . . . dated Apr. 17, 2019. 27 pages.
Non-Final Office Action for U.S. Appl. No. 14/891,306, filed Nov. 13, 2015 on behalf of Probiotical S.P.A dated May 2, 2019 25 pages.
Notice of Allowance for U.S. Appl. No. 14/116,999, filed Dec. 20, 2013, on behalf of Probiotical S.P.A. dated Dec. 26, 2018. 14 pages.
Notice of Allowance for U.S. Appl. No. 14/116,999, filed Dec. 20, 2013, on behalf of Probiotical S.p.A. dated Sep. 4, 2018. 11 pgs.
Notice of Allowance for U.S. Appl. No. 14/117,003. dated Nov. 24, 2017, 5 pages.
Notice of Allowance for U.S. Appl. No. 14/346,941, filed Mar. 24, 2014 on behalf of Giovanni Mogna. dated Aug. 6, 2018. 8 pages.
Notice of Allowance for U.S. Appl. No. 14/346,941, filed Mar. 24, 2014 on behalf of Probiotical North America Inc . . . dated Apr. 8, 2019. 29 pages.
Notification of Reexamination for Chinese Patent Application No. CN201280022854 in the name of Probiotical S.P.A, dated Sep. 29, 2018. (Chinese Original + English Translation). 14 pages.
Okombo J., et al., "Probiotic-Induced Reduction of Gastrointestinal Oxalate Absorption in Healthy Subjects," Urological Research, Jun. 2010, vol. 38 (3), pp. 169-178. 10 pages.
Peng F., et al., "Health Education for Kidney Diseases," Hubei Science & Technology Press, Dec. 31, 2007, p. 102. (Chinese Original + English Translation) 5 pages.
Rowe, R.C. et al., "Handbook of Pharmaceutical Excipients", Chemical Industry Press, 4th Edition, pp. 692-693, (Jan. 31, 2005), 9 pages. (English Translation + Chinese Original).
Russian Office Action for Russian Application No. 2015148752/15 filed on May 14, 2014 on behalf of Probiotical S.P.A. dated Apr. 24, 2018. 11 pages. (Russian original + English translation).
Schillinger U., et al., "Antibacterial Activity of Lactobacillus sake Isolated from Meat", Applied and Environmental Microbiology, Aug. 1989, vol. 55, No. 8, pp. 1901-1906.
Simone, et al. "The Probiotic Bifidobacterium breve B632 Inhibited the Growth of Enterobacteriaceae within Colicky Infant Microbiota Cultures", Hindawi Publishing Corporation, BioMed Research International, vol. 2014, article ID 301053 (Aug. 2014). 7 pages.
International Preliminary Report on Patentability for International Application No. PCT/IB2012/001741 filed Sep. 10, 2012 on behalf of Giovanni Mogna. dated Mar. 12, 2014.10 pages.
Basic Microbiology, Eighth edition. Wesley Volk and Jay Brown, eds. Addison-Wesley (1997), pp. 221, 344-345. 5 pages.
Bondarenko V. M. Molecular-cellular mechanisms of therapeutic action of probiotics. Biologicals. Prevention, diagnosis, treatment. Scientific center of expertise of medical application of the Ministry of health of the Russian Federation (Moscow) 2010 No. 1 (37) p. 31-34; 6 pages.
Botes, M., et al. "Evaluation of Enterococcus mundtii ST4SA and Lactobacillus plantarum 423 as probiotics by using a gastro-intestinal model with infant milk formulations as substrate", International Journal of Food Microbiology (Dec. 2008), 128(2), 362-370. Abstract Only.
Decision to Grant for Russian Patent Application No. 2014107771/10 filed Sep. 10, 2012 on behalf of Probiotical S.P.A. dated May 23, 2017. 11 pages. (Russian original + Partial English translation).
International Preliminary Report on Patentability for Application No. PCT/IB2012/001848 filed Sep. 21, 2012 on behalf of Probiotical S.P.A. dated Mar. 25, 2014. 4 pages. (English Only).
International Preliminary Report on Patentability for Application No. PCT/IB2014/000731 filed May 14, 2014 on behalf of Probiotical S.P.A. dated Nov. 17, 2015. 11 pages (English Only).
Japanese Office Action for Japanese Application No. 2014-529082 filed Mar. 7, 2014 on behalf of Probiotical S.P.A. dated Jul. 19, 2016. 13 pages. (Japanese Original + English Translation).
Japanese Patent Office Official Action for Japanese Patent Application No. 2016513453. dated Jan. 9, 2018. 9 pages. (Japanese original + English translation).
Japanese Patent Office Official Action Summary for Japanese Patent Application No. 2016513453 filed on behalf of Probiotical S.P.A. dated Jan. 9, 2018. 1 page. (English Translation Only).
Kaewnopparat, S., et al. "In vitro probiotic properties of Lactobacillus fermentum SK5 isolated from vagina of a healthy woman", Anaerobe (Aug. 2013), 22, 6-13. 8 pages.

(56) References Cited

OTHER PUBLICATIONS

Office Action for Japanese Patent Application No. 2016-513453 filed on behalf of Probiotical S.P.A . . . dated Jan. 9, 2018. 9 pages. (Japanese Original + English Translation).
Office Action for Russian Patent Application No. 2015148750/15 filed May 14, 2014 on behalf of Probiotical S.P.A. dated Mar. 5, 2018. 19 pages. (Russian Original + English Translation).
Russian Search Report for Russian Application No. 2015148752/15 filed on May 14, 2014 on behalf of Probiotical S.P.A. dated Apr. 20, 2018. 4 pages. (Russian original + English translation).
International Preliminary Report on Patentability for International Application No. PCT/IB2012/000779 filed Apr. 18, 2012 on behalf of Giovanni Mogna. dated Oct. 22, 2013. 6 pages.(English Only).
Russian Patent Office Official Action for Russian Patent Application No. 2015148752/15 filed on behalf of Probiotical S.P.A. dated Apr. 24, 2018. 11 pages. (Russian original + English translation).
"The Language of Prevention" from National Public Health Partnership, 2006. Melbourne: NPHP. 9 pages.
Wikipedia definition of p-value (printed on Jul. 3, 2018) 12 pages. https://en.wikipedia.org/wiki/P-value.
"Study on Optimization of Exopolysaccharide and Characteristics of *Streptococcus thermophilus* ST1," 2011. 73 pages. (7-8). (English Abstract Only).
Wang Q., et al., "Urinary Tract Infections," Shanghai Liandong Press, Jul. 31, 2001, p. 4 (original + English translation). 5 pages.
Wikipedia entry for "yeast", dated Mar. 1, 2011 (13 pages).
Grill, J.P., et al., "Bile Salt Toxicity to Some Bifidobacterial Strains: Role of Conjugated Bile Salt Hydrolase and pH," *Canadian Journal of Microbiology*, 46, pp. 878-884.Oct. 2000. 7 Pages.
Klaver, F., et al., "The Assumed Assimilation of Cholesterol by Lactobacilli And Bifidobacterial Bifidum is Due To Their Bile Salt-Deconjugating Activity," *Appl Environ Microbiology*,vol. 59, No. 4, pp. 1120-1124.1993. 5 Pages.
Losada, M.A., et al., "Towards A Healthier Diet for The Colon: The Influence of Fructooligosaccharides and Lactobacilli on Intestinal Health," Nutrition Research, vol. 22, pp. 71-84. 2002. 14 Pages.
Non-Final Office Action for U.S. Appl. No. 15/902,977, filed Feb. 22, 2018 on behalf of Hoffmann-Eitle SRL. dated Oct. 31, 2019. 20 pages.
Restriction Requirement for U.S. Appl. No. 16/368,655, filed Mar. 28, 2019 in the name of Probiotical S.P.A. dated Oct. 10, 2019. 7 pages.
Bifisterol Class IIA Medical Device for Oral Use Pamphlet/ Packaging from http://www.probiotical.com. 2 pages. 2015.
Bifisterol Probiotic Product Pamphlet from http://www.probiotical. com. 2 pages 2015.
Brazilian Office Action for Brazilian Application No. BR112013028496-0 dated Oct. 17, 2019 on behalf of Probiotical S.P.A., 5 pages. Brazilian + English translation.
Brazilian Office Action for Brazilian Application No. BR112013028705-5 dated Aug. 14, 2019 on behalf of Probiotical S.P.A., 6 pages. Brazilian + English translation.
Brazilian Patent Office Official Action for Brazilian Patent Application No. BR112015027536-2 filed on behalf of Probiotical S.P.A., dated Oct. 2, 2019, 6 pages. (Brazilian + English translation).
Examination Report for Indian Application No. 8722/CHENP/2013 filed on behalf of Probiotical S.P.A. dated Jul. 5, 2018. 8 Pages. (Hindi + English Translation).
Final Office Action for U.S. Appl. No. 14/113,211, filed Nov. 26, 2013 on behalf of Giovanni Mogna. dated Mar. 4, 2020. 25 pages.
Hearing Notice for Indian Application No. 8722/CHENP/2013 filed on behalf of Probiotical S.P.A. Date of Dispatch: Oct. 17, 2019. 3 Pages. (Hindi+ English Translation).
Japanese Patent Office Decision to Grant for Japanese Patent Application No. 2016-513453 filed on behalf of Probiotical S.P.A, certification date Sep. 3, 2019, dated Sep. 10, 2019. 7 pages. (Japanese + English translation).
Non-Final Office Action for U.S. Appl. No. 16/368,655 filed on behalf of Probiotical S.p.A. dated Mar. 2, 2020. 22 pages.
Notice of Allowance for U.S. Appl. No. 14/891,306, filed Nov. 13, 2015 on behalf of Probiotical S.P.A. dated Jan. 13, 2020. 15 pages.
Notice of Allowance for U.S. Appl. No. 15/902,977, filed Feb. 22, 2018 on behalf of Probiotical S.P.A. dated Apr. 23, 2020. 5 Pages.
Notification of Reexamination for Japanese Patent Application No. JP2014509850 in the name of Probiotical S.P.A, dated Feb. 16, 2016. (Japanese Original + English Translation). 5 pages.
Preliminary office Action for Brazilian Application No. BR112013028709-8 filed on May 9, 2012 on behalf of Probiotical S.P.A. dated Aug. 13, 2019. 5 Pages. (Portuguese and Informal English Translation).
Bozzi Cionci, N., et al., "Therapeutic Microbiology: The Role of Bifidobacterium breve as Food Supplement for the Prevention/ Treatment of Paediatric Diseases," *Nutrients*, 10, 1723, Published: Nov. 10, 2018. 27 Pages.
Final Office Action for U.S. Appl. No. 16/368,655, filed Mar. 28, 2019 on behalf of Probiotical S.P.A. dated Jul. 14, 2020 14 pages.
Notice of Allowance for U.S. Appl. No. 14/891,306, filed Nov. 13, 2015 on behalf of Probiotical S.P.A. dated May 22, 2020 11 pages.
Decision of Rejection for Chinese Application No. 201280031191. 7, dated May 12, 2020, with English translation. 14 pages.
Notice of Allowance for U.S. Appl. No. 14/891,306, filed Nov. 13, 2015 on behalf of Probiotical S.P.A. dated Aug. 5, 2020. 9 Pages.
Corrected Notice of Allowability for U.S. Appl. No. 14/891,306, filed Nov. 13, 2015 on behalf of Probiotical S.P.A. dated Aug. 20, 2020. 5 pages.
Canadian Office Action for CA Application No. 2,912,013 filed on May 14, 2014 on behalf of Probiotical S.P.A. dated Aug. 24, 2020. 4 pages.
Korean Office Action for KR Application No. 1020157035288 filed on May 14, 2014 on behalf of Probiotical S.P.A. dated Aug. 11, 2020 8 pages (English + Original).
Notice of Allowance for U.S. Appl. No. 15/902,977, filed Feb. 22, 2019 on behalf of Giovanni Mogna dated Oct. 13, 2020 17 pages.
Notice of Allowance (Technical Examination Report) dated Sep. 14, 2020, published in Brazilian Industrial Property Journal of Sep. 29, 2020 for Brazilian Application No. BR112013028709-8 filed on May 9, 2012 on behalf of Probiotical S.P.A. 5 Pages. (Portuguese + partial Eng trans.).
Brazilian Office Action for Brazilian Application No. BR112013028496-0 filed May 9, 2012, on behalf of Probiotical S.P.A. dated Oct. 6, 2020. Portuguese Original + English Translation. 12 Pages.
Notice of Allowance for U.S. Appl. No. 14/891,306, filed Nov. 13, 2015 on behalf of Probiotical S.P.A. dated Jan. 15, 2021. 11 Pages.
Notice of Allowance for U.S. Appl. No. 15/902,977, filed Feb. 22, 2018 on behalf of Probiotical S.P.A. dated Jan. 25, 2021. 6 pages.
Brazilian Office Action for Brazilian Application No. BR112013028705-5 dated Dec. 14, 2020 on behalf of Probiotical S.P.A., 8 pages. Brazilian + partial English translation.
Decision to Grant for Indian Patent No. 358118, Application No. 1949/MUMNP/2013 filed on May 9, 2012 on behalf of Probiotical S.P.A. Granted on Feb. 9, 2021. 28 pages.

\* cited by examiner

Figure 1 A-B
A)
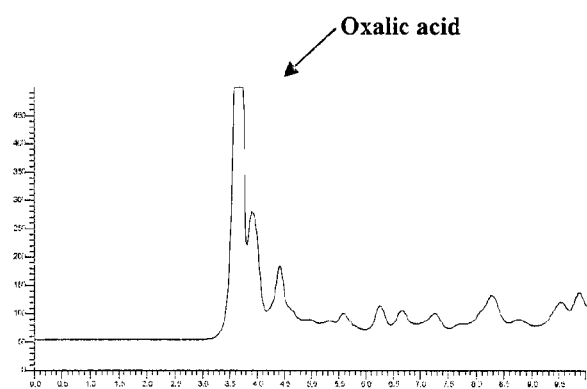
B)
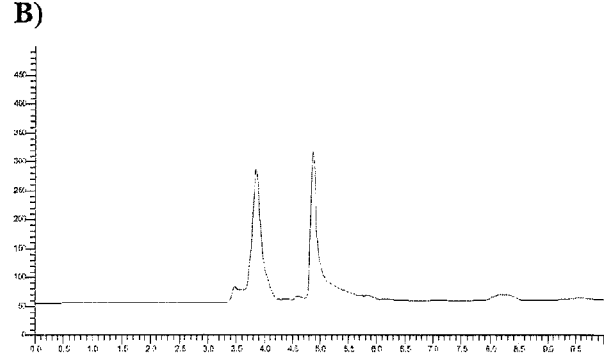
Fig. 1: Comparison between the chromatogram for the culture medium containing 5 mM of oxalate before (A) and after (B) SPE purification.

Fig. 2: Chromatogram for the culture medium containing 5 mM of oxalate (Positive reference).

Fig. 3: Chromatogram for the bacterial strain *B. breve* BR03 DSM 6604.

Fig. 4: Chromatogram for the bacterial strain *L. paracasei spp. paracasei* LPC 09 DSM 24243.

Acidification curves

BACTERIAL STRAINS CAPABLE OF METABOLIZING OXALATES

CROSS REFERENCE TO RELATED APPLICATIONS

The present application is the US national stage of International Patent Application PCT/IB2012/000895 filed on May 9, 2012 which, in turn, claims priority to Italian Patent Application MI2011A000791 filed on May 9, 2011.

The present invention relates to a selection of lactic bacterial strains and bifidobacteria of human intestinal origin capable of metabolizing oxalic acid and/or the salts thereof (oxalates). Moreover, the present invention relates to a food composition or supplement product or medical device or pharmaceutical composition containing said bacterial strains.

Oxalate (salt of oxalic acid) is an ubiquitous compound in the plant kingdom, widely present in all human diets. The daily intake ranges from 70 to 920 mg (average 495 mg~5.6 mM), but these values are easily exceeded in the diets of vegetarians.

Oxalic acid (dicarboxylic acid) is one of the most highly oxidized organic compounds and thus acts as a powerful chelating agent for cations, in particular the ion $Ca^{2+}$. Because of this property, the salts of oxalic acid (oxalates) are of very little use in catabolic processes and energy production. Moreover, oxalic acid is toxic for the majority of living beings and particularly for mammals.

For this reason, the accumulation of oxalic acid and oxalates in man can trigger and exacerbate a series of pathological conditions, among which we shall mention hyperoxaluria, urolithiasis, kidney failure, cardiomyopathies and other cardiac disorders. In particular, oxalic acid combines with calcium to form the corresponding calcium oxalate, an insoluble salt which is responsible for over 70% of the kidney stones diagnosed. Moreover, oxalic acid is a powerful inflammatory agent affecting the intestinal mucosa. Therefore, an excess presence of this acid in the lumen can compromise the natural barrier function of the epithelium by altering its permeability and consequently provoking an increased absorption of oxalate. In particular, the colon is the main site of absorption of oxalate, with an intake of 3-5% in normal physiological conditions. Reducing the oxalate in the intestinal lumen could therefore contribute to reducing absorption. This would then lead to a decrease in the concentration of oxalates in plasma and in urine, thus reducing the hazardousness thereof.

Moreover, high levels of oxalates in the blood can lead to diverticulosis or diverticulitis. Diverticulosis, also known as "diverticular disease", is a medical condition characterized by diverticula in the colon; these are eversions of the mucosa and submucosa of the colon through areas of relative weakness of the muscular layer in the wall of the colon. Diverticula are decidedly more common in the sigmoid colon, which is a portion of the intestine characterized by greater pressure, a factor facilitating the formation of diverticula. Diverticulitis is a pathology of the digestive tract, characterized by the inflammation of one or more diverticula. The majority of cases of diverticulitis are localized in the colon (in particular the descending and sigmoid colon).

Therefore, it is important to be able to reduce the amount of oxalates in the intestinal lumen, plasma and urine in such a way as to avoid the complications connected with high values of oxalates, such as, for example, hyperoxaluria, urolithiasis, kidney failure, cardiomyopathies and other cardiac disorders, kidney stones, diverticulosis and diverticulitis.

In particular, it is desirable to be able to reduce the levels of oxalate in the urine of two types of subjects:
- Hyperoxaluric subjects who do not tend toward a diet with a high oxalate content.
- Normooxaluric subjects who tend toward to a diet with a high oxalate content.

The Applicant has provided an answer to the abovementioned needs following an intense activity of research, at the end of which it identified, from a highly vast set of strains, a selection of bacterial strains belonging to the genera *Lactobacillus* and *Bifidobacterium*; said strains exhibit a marked ability to quantitatively degrade oxalates. The selected strains show the ability to use oxalate as a source of energy, removing it from the environment in which said oxalate was originally to be found. Therefore, the selected strains are capable of degrading oxalates.

The subject matter of the present invention relates to a bacterial strain belonging to the genera *Lactobacillus* and *Bifidobacterium* and having the ability to degrade oxalates, as disclosed in the appended independent claim.

The subject matter of the present invention also relates to a food composition or supplement product or medical device or pharmaceutical composition containing said bacterial strains, as disclosed in the appended independent claim.

Preferred embodiments of the present invention will be illustrated in the detailed description that follows.

FIG. 1 shows a comparison between the chromatogram for a culture medium containing 5 mM of oxalate before (A) and after (B) SPE purification.

Figure 2:
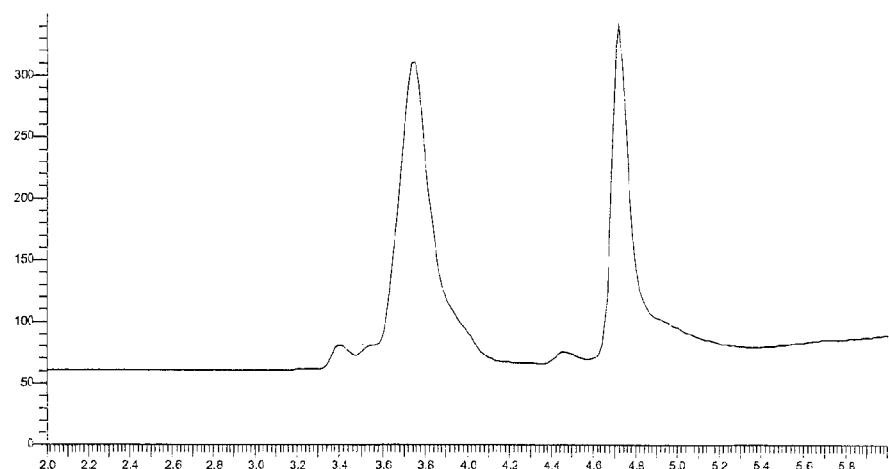
FIG. 2 shows a chromatogram for a culture medium containing 5 mM of oxalate (positive reference).
Figure 3:
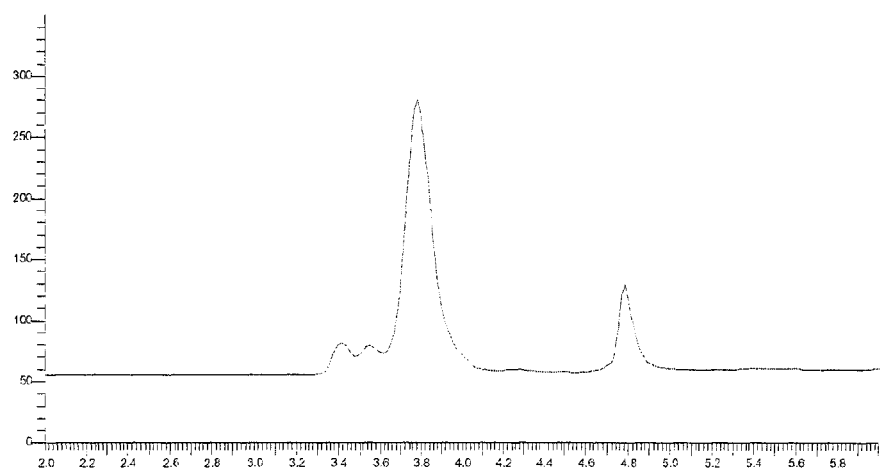
FIG. 3 shows a chromatogram for the bacterial strain *B. breve* BRO3 DSM 16604.
Figure 4:
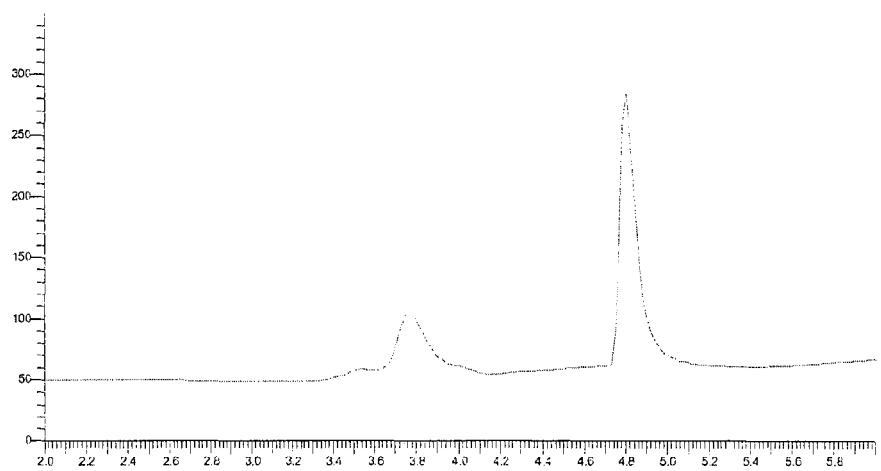
FIG. 4 shows a chromatogram for the bacterial strain *L. paracasei* spp. *paracasei* LPC09 DSM 24243.

The Applicant has developed a method capable of identifying and quantifying the oxalate degrading ability of cultures of strains belonging to the genera *Lactobacillus* and *Bifidobacterium*.

The Applicant has found that the following bacterial strains have a demonstrated ability to use oxalates as an energy source:

(i) *L. paracasei* spp. *paracasei* LPC 09, deposited by the company Probiotical SpA of Novara (Italy) on 23 Nov. 2010, with deposit number DSM 24243.

(ii) *L. gasseri* LGS 01, deposited by the company Probiotical SpA of Novara (Italy) on 24 May 2006, with deposit number DSM 18299.

(iii) *L. crasseri* LGS 02, deposited by the company Probiotical SpA of Novara (Italy) on 24 May 2006, with deposit number DSM 18300.

(iv) *L. acidophilus* LA 07, deposited by the company Probiotical SpA of Novara (Italy) on 23 Nov. 2010, with deposit number DSM 24303.

(v) *L. acidophilus* LA 02, deposited by the company Probiotical SpA of Novara (Italy) on 6 Aug. 2008, with deposit number DSM 21717.

(vi) *L. plantarum* LP 01, deposited by the company Mofin Srl of Novara (Italy) with the Depositary Institution BCCM-LMG (Belgium) on 16 Oct. 2001, with deposit number LMG-P-21021, (vii) *L. reuteri* LRE 03, deposited by the company Probiotical SpA of Novara (Italy) on 5 Aug. 2010, with deposit number DSM 23879.

(viii) *L. reuteri* LRE 02, deposited by the company Probiotical SpA of Novara (Italy) on 5 Aug. 2010, with deposit number DSM 23878.

(ix) *B. breve* BR 03, deposited by the company Probiotical SpA of Novara (Italy) on 16 Jul. 2004, with deposit number DSM 16604.

(x) *B. longum* BL 03, deposited by the company Probiotical SpA of Novara (Italy) on 20 Jul. 2004, with deposit number DSM 16603.

(xi) *L. rhamnosus* GG, ATCC 53103, available in the ATCC public collection.

(xii) *L. reuteri* LRE 04, deposited by the company Probiotical SpA of Novara (Italy) on 5 Aug. 2010, with deposit number DSM 23880.

(xiii) *L. rhamnosus* LR 06, deposited by the company Probiotical SpA of Novara (Italy) on 14 Nov. 2008, with deposit number DSM 21981.

(xiv) *B. lactis* BA 05, deposited by the company Probiotical SpA of Novara (Italy) on 15 Jun. 2006, with deposit number DSM 18352.

(xv) *L. casei* spp. *rhamnosus* LR 04, deposited by the company Probiotical SpA of Novara (Italy) on 20 Jul. 2004, with deposit number DSM 16605.

In a preferred embodiment, the composition comprises or, alternatively, consists of at least one strain selected from among those indicated above by (i) to (xv); preferably the strains are selected from among those indicated above by (i) to (viii).

In the context of the present invention, "bacterial strain" means the live and/or dead cells and/or parts, components/derivatives and/or enzymes thereof.

The selected bacterial strains belong to the genus *Lactobacillus* and have an ability to degrade and use oxalate as a source of energy in an amount greater than 50%.

Advantageously, said ability is greater than 60%. Advantageously, said ability is greater than 70%.

The selected bacterial strains belong to the species *Lactobacillus paracasei*. A preferred strain is *L. paracasei* spp. *paracasei* LPC 09 DSM 24243.

The selected bacterial strains belong to the species *Lactobacillus gasseri*. Several preferred strains are selected from the group comprising or, alternatively, consisting of *L. gasseri* LGS 01 DSM 18299 and *L. gasseri* LGS 02 DSM 18300.

The selected bacterial strains belong to the species *Lactobacillus acidophilus*. Several preferred strains are selected from the group comprising or, alternatively, consisting of *L. acidophilus* LA02 DSM 21717 and *L. acidophilus* LA 07 DSM 24303.

A composition in accordance with the present invention comprises at least one bacterial strain, for use in the treatment of hyperoxaluria, urolithiasis, kidney failure, cardiopathies, kidney stones, diverticulosis and diverticulitis.

The composition can be a food composition or supplement product or medical device or pharmaceutical composition.

The composition for use in the treatment of hyperoxaluria, urolithiasis, kidney failure, cardiopathies, kidney stones, diverticulosis and diverticulitis comprises or, alternatively, consists of at least two strains selected from among those indicated above by (i) to (xv), preferably the strains are selected from among those indicated above by (i) to (viii).

The composition for use in the treatment of hyperoxaluria, urolithiasis, kidney failure, cardiopathies, kidney stones, diverticulosis and diverticulitis comprises or, alternatively, consists of at least two strains selected from among those indicated above by (i) to (v).

The composition for use in the treatment of hyperoxaluria, urolithiasis, kidney failure, cardiopathies, kidney stones, diverticulosis and diverticulitis comprises or, alternatively, consists of:

(a) *L. paracasei* spp. *paracasei* LPC 09 -DSM 24243; or (b) *L. paracasei* spp. *paracasei* LPC 09 -DSM 24243 and *L. gasseri* LGS 01 -DSM 18299; or (c) *L. paracasei* spp. *paracasei* LPC 09 -DSM 24243 and *L. gasseri* LGS 02 -DSM 18300; or (d) *L. paracasei* spp. *paracasei* LPC 09 -DSM 24243, *L. gasseri* LGS 01 -DSM 18299 and *L. gasseri* LGS 02 -DSM 18300; or (e) *L. paracasei* spp. *paracasei* LPC 09 -DSM 24243, *L. gasseri* LGS 01 -DSM 18299, *L. gasseri* LGS 02 -DSM 18300 and *L. acidophilus* LA 07 -DSM 24303; or (f) *L. paracasei* spp. *paracasei* LPC 09 -DSM 24243, *L. gasseri* LGS 01 -DSM 18299, *L. gasseri* LGS 02 -DSM 18300 and *L. acidophilus* LA 02 -DSM 21717; or (g) *L. paracasei* spp. *paracasei* LPC 09 -DSM 24243, *L. gasseri* LGS 01 -DSM 18299, *L. gasseri* LGS 02 -DSM 18300, *L. acidophilus* LA 07 -DSM 24303 and *L. acidophilus* LA 02 -DSM 21717.

All of the above-described compositions, and particularly the compositions (a) to (g) listed above, can further comprise fructo-oligosaccharides (FOS) and/or inulin. Fructo-oligosaccharides (FOS) and/or inulin are included in an amount comprised from 1 to 30% by weight, relative to the weight of the composition, preferably from 3 to 15%, even more preferably from 5 to 10% by weight.

The subject matter of the present invention relates to a bacterial strain belonging to the species *Lactobacillus paracasei* or *Lactobacillus gasseri* and which is capable of degrading oxalic acid and/or the salts thereof in an amount greater than 60%. Said strain is capable of degrading oxalic acid and/or the salts thereof in an amount greater than 70%. Said strain belonging to the species *Lactobacillus paracasei* is *L. paracasei* spp. *paracasei* LPC 09 DSM 24243. Said strain belonging to the species *Lactobacillus gasseri* is selected from the group comprising the strain *L. gasseri* LGS 01 DSM 18299 and the strain *L. gasseri* LGS 02 DSM 18300. Said strain belonging to the species *Lactobacillus gasseri* is selected from the group consisting of the strain *L. gasseri* LGS 01 DSM 18299 and the strain *L. gasseri* LGS 02 DSM 18300.

The subject matter of the present invention relates to a food composition or supplement product or medical device or pharmaceutical composition comprising a bacterial composition; said bacterial composition comprises at least one bacterial strain as described above, for use in the preventive and curative treatment of hyperoxaluria, urolithiasis, kidney failure, cardiopathies, kidney stones, diverticulosis and diverticulitis. Said bacterial composition comprises the strain *L. paracasei* spp. *paracasei* LPC 09 DSM 24243. Said bacterial composition comprises the strain *L. gasseri* LGS 01 DSM 18299 and the strain *L. gasseri* LGS 02 DSM 18300. Said bacterial composition further comprises the strain *L. acidophilus* LA02 DSM 21717 and the strain *L. acidophilus* LA 07 DSM 24303. Said bacterial composition consists of *L. paracasei* spp. *paracasei* LPC 09 DSM 24243, *L. acidophilus* LA02 DSM 21717 and/or *L. acidophilus* LA 07 DSM 24303. Said composition further comprises fructo-oligosaccharides and/or inulin.

Experimental Part

1. Bacterial Strains Analyzed

About 70 strains belonging to the genera *Bifidobacterium* and *Lactobacillus* were studied; they came from the internal strain collection of the company Probiotical SpA of Novara and international collections such as, for example, the DSMZ-Germany, or were found in the literature. The selected strains are shown in Table 1, which shows the percentage of oxalate degradation by the bacterial strains tested. The experiment was conducted using a culture medium containing 5 mM ammonium oxalate.

TABLE 1

| Deposit No. | Species/strain | % Degradation |
| --- | --- | --- |
| DSM 24243 | *L. paracasei* LPC 09 | 73.50 |
| DSM 18299 | *L. gasseri* LGS 01 | 73.40 |
| DSM 18300 | *L. gasseri* LGS 02 | 71.20 |
| DSM 24303 | *L. acidophilus* LA 07 | 59.25 |
| DSM21717 | *L. acidophilus* LA 02 | 56.35 |
| LMG P-21021 | *L. plantarum L LP 01* | 40.31 |
| DSM 23879 | *L. reuteri* LRE 03 | 33.86 |
| DSM 23878 | *L. reuteri* LRE 02 | 31.42 |
| DSM 16604 | *B. breve* BR 03 | 28.16 |
| DSM 16603 | *B. longum* BL 03 | 25.29 |
| ATCC 53103 | *L. rhamnosus* GG | 23.59 |
| DSM 23880 | *L. reuteri* LRE 04 | 16.79 |
| DSM 21981 | *L. rhamnosus* LR 06 | 15.70 |
| DSM 18352 | *B. lactis* BA 05 | 15.45 |
| DSM 16605 | *L. rhamnosus* LR 04 | 12.89 |

The bacterial strains (i) to (v), (vii) to (x) and (xii) to (xv) listed in Table 1 were deposited by the company Probiotical SpA of Novara (Italy). Strain (vi) was deposited by the company Mofin Srl cf Novara (Italy). Strain (xi) is available from the ATCC collection. All strains are available and accessible to the public under the conditions established by the Budapest Treaty.

2. Culture Conditions Adopted

The preparation of the strains to be submitted to analysis consisted in a series of three sequential subcultures in MRS broth (+1% cys-HCl, anaerobiosis, for the bifids) incubated at 37° C. until adequate growth was reached. This culture strategy enables complete activation of the strain. The strains were subsequently inoculated at the same percentage of inoculum (2%) in an experimental medium, specifically conceived to ensure maximum growth of lactobacilli and bifidobacteria, supplemented with 5 mM ammonium oxalate (amount equal to the average daily intake of oxalic acid). The cultures thus prepared were incubated for 24 hours at 37° C.

3. SPE (Solid Phase Extraction) Purification of the Samples

At the end of the incubation period, the broth cultures were centrifuged and the supernatant was filtered through a 0.22 µm filter. HPLC injection of the samples brought to light an unclear chromatographic profile. In particular, the chromatographic peak of oxalic acid appeared to overlap the glucose peak present in the samples. In order to remedy the aforesaid problem, the samples were purified using SPE (solid phase extraction) columns specific for organic acids. The protocol for purification by SPE columns required an optimization step in order to obtain the best final yield. In particular, different reagents were used in relation to the column conditioning step and final elution of the analyte. This solid-phase purification made it possible to obtain a distinctly cleaner chromatographic peak of oxalic acid, as can be seen in FIG. 1A-B. The protocol used was the following Type of SPE column: Phenomenex Strata-XA
Activation: 1 ml of methanol
Conditioning: 2 ml of sodium formiate 20 mM
Sample loading: 1 ml sample
Washing of impurities: 1 ml ammonium acetate 25 mM+1 ml methanol
Elution: 2×500 µl HCl M+2×500 µl HCl 3 M 4. HPLC Analysis The amount of oxalate degraded by each individual strain was analyzed by HPLC, calculating the difference between the concentration of oxalate present in the culture medium (5 mM) at T0 (before fermentation) and the residual concentration after growth of the microorganism. The results of the individual strains are expressed as percentages, considering the concentration of oxalate at T0 to be 100. For example, the result of the strain *L. paracasei* spp. *paracasei* LPC 09 DSM 24243, equal to around 70%, indicates that the latter is able to use an amount of oxalate equal to around 3.5 mM of oxalate (70% of 5 mM). The HPLC protocol used was the following:

Type of column: Phenomenex Hydro-RP 250×4.6 mm
Type of detector: UV-Vis with reading at 220 nm
Elution flow rate: 0.7 ml/min
Injection volume: 20 µl
Column temperature: 30° C.
Type of elution: isocratic
Mobile phase: 20 mM Potassium phosphate pH 2.0

The bacterial strains belonging to the genus *Lactobacillus* which showed a high degradation activity towards oxalic acid are the ones indicated above by (i) to (v).

A. Determination of the Acidification Curves for the Strain *L. paracasei* spp. *paracasei* LPC 09 DSM 24243.

The strain LPC09 was reactivated prior to the experiment by subculture in MRS and incubated under aerobiosis at 37° C. The reactivation steps were repeated three times prior to the experiment with overnight incubation. At the end of the third reactivation step, the cells were pelleted, washed with sterile water and resuspended before being inoculated into the culture media supplemented with fibre. The media used were based on sugar-free MRS (carbon sources), supplemented respectively with:

Glucose (solution sterilized by heat treatment, 121° C. 15'), control medium.
Fructo-oligosaccharides—FOS (solution sterilized by filtration, 0.20 µl filter).
GOS-Gal,—Galacto-oligosaccharides with glucose residual (solution sterilized by filtration, 0.20 µl filter).
GOS-Gal,—Galacto-oligosaccharides with galactose residual (solution sterilized by filtration, 0.20 µl filter).
XOS,—xylo-oligosaccharides (solution sterilized by filtration, 0.20 µl filter).
Larex,—larch fibre (solution sterilized by heat treatment, 121° C. 15').
Inulin (solution sterilized by heat treatment, 121° C. 15').

The final concentration of carbon sources for all media was 20 g/l.

The media thus prepared were then inoculated with the strain LPC09, at a percentage of 4%, and incubated at 37° C. under aerobiosis.

Figure 5:
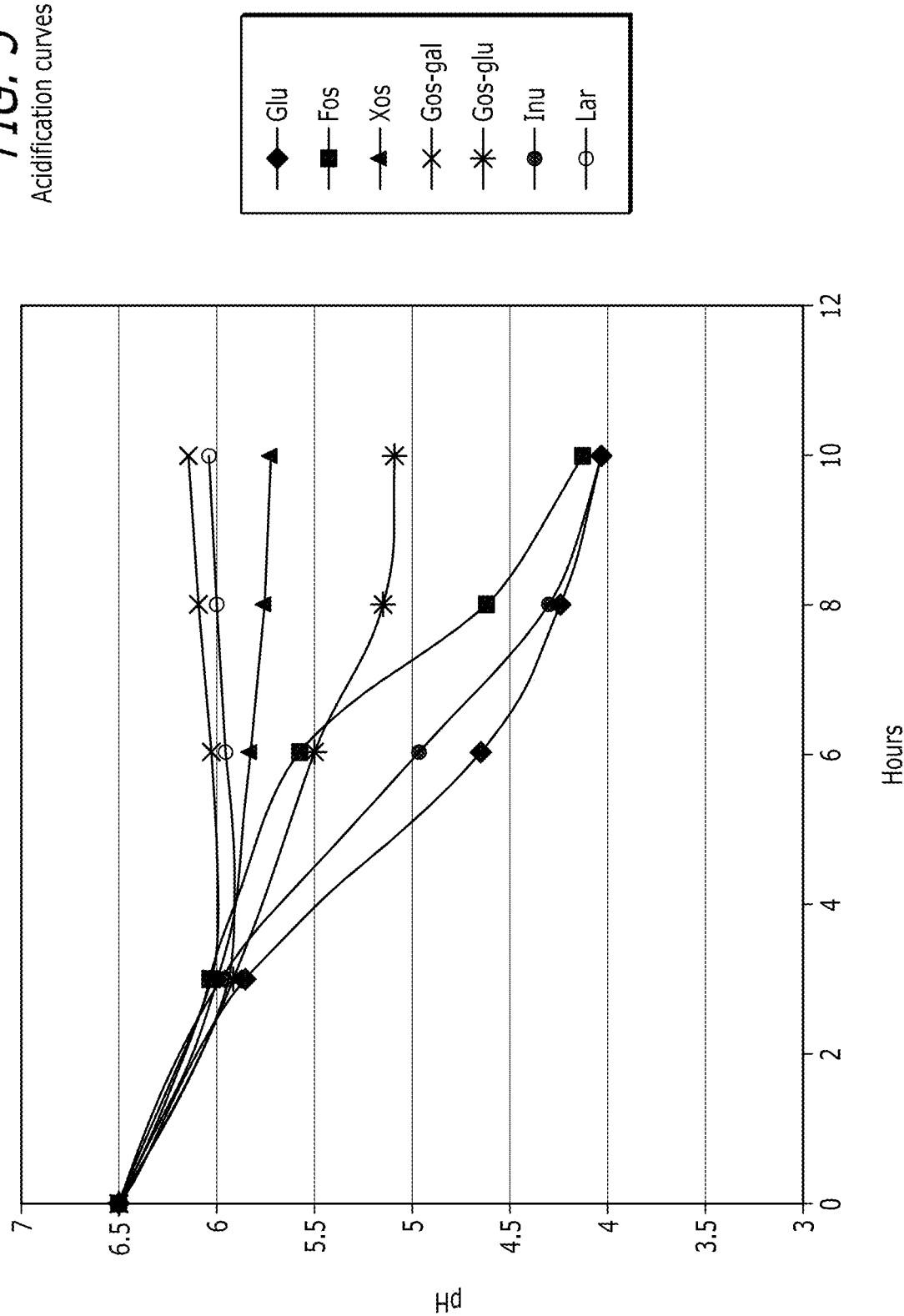
FIG. 5 shows acidification curves (pH value) obtained as a function of time (T=0, 3, 6, 8 and 10 hours) when the strain *L. paracasei* spp. *paracasei* LPC 09 DSM 24243 was made to grow in a sugar-free MRS culture medium (carbon source), to which other carbon sources (fibres) were respectively added.

At time 0 and at 3, 6, 8 and 10 hours, pH measurements were made in order to construct the acidification curves shown in the graph of FIG. 5.

Table 2 shows the acidification curves (pH value) obtained as a function of time (T=0, 3, 6, 8 and 10 hours)

when the strain the *L. paracasei* spp. *paracasei* LPC 09 DSM 24243 was made to grow in a culture medium as described above.

TABLE 2

|  |  | 0 | 3 | 6 | 8 | 10 |
|---|---|---|---|---|---|---|
| LPC09 | Glu | 6.46 | 5.84 | 4.65 | 4.24 | 4.03 |
|  | Fos | 6.48 | 6.02 | 5.57 | 4.62 | 4.13 |
|  | Xos | 6.47 | 5.98 | 5.83 | 5.76 | 5.73 |
|  | Gos-gal | 6.48 | 6.03 | 6.02 | 6.09 | 6.14 |
|  | Gos-glu | 6.49 | 5.9 | 5.5 | 5.14 | 5.09 |
|  | Inu | 6.5 | 5.98 | 4.96 | 4.3 | 4.03 |
|  | Lar | 6.43 | 5.93 | 5.95 | 5.99 | 6.03 |

The invention claimed is:

1. A method for preventive and/or curative treatment in a subject of hyperoxaluria, urolithiasis, kidney failure, cardiopathies, kidney stones, diverticulosis and diverticulitis, the method comprising
administering to the subject a food composition or supplement product or medical device or pharmaceutical composition comprising a bacterial composition, said bacterial composition comprising the strain *L. paracasei* spp. *paracasei* LPC 09 DSM 24243.

2. The method according to claim 1, wherein the composition further comprises at least one bacterial strain selected from the group consisting of the bacterial strain *L. gasseri* LGS 01 DSM 18299 and the bacterial strain *L. gasseri* LGS 02 DSM 18300.

3. The method according to claim 1, wherein the composition further comprises bacterial strain *L. acidophilus* LA02 DSM 21717 and the bacterial strain *L. acidophilus* LA 07 DSM 24303.

4. The method according to claim 1, wherein the composition further comprises fructo-oligosaccharides and inulin.

5. The method according to claim 1, wherein said bacterial composition consists of *L. paracasei* spp. *paracasei* LPC 09 DSM 24243, *L. acidophilus* LA02 DSM 21717 and *L. acidophilus* LA 07 DSM 24303.

6. The method according to claim 2, wherein the composition further comprises fructo-oligosaccharides and inulin.

* * * * *